(12) United States Patent
Perregaard et al.

(10) Patent No.: US 6,767,907 B2
(45) Date of Patent: Jul. 27, 2004

(54) 4-ARYL-1-(INDANMETHYL DIHYDROBENZOFURANMETHYL OR DIHYDROBENZOTHIOPHENEMETHYL) PIPERIDINES TETRAHYDROPYRIDINES OR PIPERAZINES

(75) Inventors: Jens Kristian Perregaard, Jaegerspris (DK); John Willie Stenberg, Copenhagen (DK); Bitten Hansen, Koge (DK)

(73) Assignee: H. Lundbeck A/S, Copenhagen-Valby (DK)

( * ) Notice: Subject to any disclaimer, the term of this patent is extended or adjusted under 35 U.S.C. 154(b) by 0 days.

(21) Appl. No.: 09/549,861

(22) Filed: Apr. 14, 2000

(65) Prior Publication Data
US 2003/0195356 A1 Oct. 16, 2003

Related U.S. Application Data

(63) Continuation of application No. 08/999,868, filed on Dec. 9, 1996, now Pat. No. 6,218,394, which is a continuation of application No. PCT/DK95/00230, filed on Jun. 8, 1995.

(30) Foreign Application Priority Data

Jun. 8, 1994 (DK) ............................................. 0649/94

(51) Int. Cl.$^7$ .................... A61K 31/496; C07D 405/06; C07D 405/14
(52) U.S. Cl. ............................ 514/253.11; 514/253.09; 514/253.01; 514/252.2; 514/210.2; 514/210.02; 514/226.8; 514/227.2; 514/228.8; 514/211.8; 514/212.01; 514/212.02; 514/212.03; 514/212.08; 514/215; 540/553; 540/488; 540/524; 540/544; 540/598; 544/373; 544/295; 544/376
(58) Field of Search ....................... 514/253.11, 253.09, 514/253.01, 210.2, 227.2, 210.02, 212.03; 540/553, 544; 544/373

(56) References Cited

U.S. PATENT DOCUMENTS 5,194,437 A 3/1993 Peglion et al. .............. 514/254

FOREIGN PATENT DOCUMENTS

| EP | 428437 A1 | 5/1991 |
| EP | 483772 | 6/1992 |
| EP | 490772 A1 | 6/1992 |

OTHER PUBLICATIONS

93–83841/10 Apr. 23, 1992 Derwent Abstract.
Chabot et al., "Bidirectional modulation off AMPA receptor propertles by exogenous phospholipase A2 in the hippocampus," Hippocampus, vol. 8, No. 3, MEDLINE abstract provlded, pp. 299–309, 1998.

Dubovsky, Beyond the serotonin reuptake inhibitors: rationales for the develpment of new serotonerglc agents,; J. Clin. Psychiatry, vol. 55, MEDLINE abstract provlded, pp. 34–44, 1994.

Gelders, "Thymosthenic Agents, A Novel Approach in the Treatment of Schizophrenia," British Journal of Psychiatry 155 (suppl. 5): 33–36 (1989).

Hyttel et al., Neurochemical Profile in Vitro of Irindalone: A $5HT_2$–Receptor Antagonist,Drug Development Research 15, pp. 389–404 (1988).

Linnoila et al., "Impulse control disorders," International Clinical Psychopharmacology, 8 Suppl. 1, pp 53–56 (1993).

Maclouf et al., "Consequences of transcellular bioxynthesis of leukotrience C4 on organ function," Haemostasis, vol. 26, Suppl. 4, MEDLINE abstract provided, pp. 28–36.

Meert et al., "The Psychopharmacology of ritanserin: comparison with chlordiazepoxide," Drug Dev. Res. 18:119–144 (1989).

Olivier et al., "Preclinical evidence on the psychotropic profile of fluvoxamine," Pharmacopsychiatry, vol. 28, Suppl. 1, MEDLINE abstract provided, pp. 2–9.

Prehn et al., "Neuroprotective properties of $5HT_{1A}$ receptor agonists in rodent models of focal and global cerebral ischemia," European Journal of Pharmacology 203:213–222 (1991).

Saxena, "Serotonin Receptors: Subtypes, Functional Responses and Therapeutic Relevance," Pharmac. Ther. vol. 66, pp. 339–368, 1995.

*Primary Examiner*—John M. Ford
(74) *Attorney, Agent, or Firm*—Darby & Darby

(57) ABSTRACT

4-Aryl-1-(indanmethyl, dihydrobenzofuranmethyl or dihydrobenzothiophenemethyl)piperidine, -tetrahydropyridine or -piperazine compounds of general formula (I), wherein one of X and Y is $CH_2$ and the other one is $CH_2$, O or S; Z is N, C, CH or COH; Ar is an optionally substituted aryl group; $R^1$ is hydrogen, alkyl, cycloalkyl, cycloalkylalkyl, aryl, arylalkyl, acyl, thioacyl, alkylsulfonyl, trifluoromethylsulfonyl, arylsulfonyl, a group $R^9VCO$— where V is O or S and $R^9$ is alkyl or aryl, or a group $R^{10}R^{11}NCO$— or $R^{10}R^{11}NCS$— wherein $R^{10}$ and $R^{11}$ are hydrogen, alkyl or aryl, or $R^{10}$ and $R^{11}$ are linked to form a ring; $R^2$ is hydrogen, alkyl, cykcloalkyl or cycloalkylalkyl; or $R^1$ and $R^2$ are linked to form a ring; $R^3$–$R^5$ are hydrogen, halogen, alkyl, alkylcarbonyl, phenylcarbonyl, alkoxy, alkylthio, hydroxy, alkylsulfonyl, cyano, trifluoromethyl, cycloalkyl, cycloalkylalkyl or nitro; $R^6$ and $R^7$ are hydrogen or alkyl or they are linked to constitute 3–7 membered ring; $R^8$ is hydrogen or alkyl; have effects at central serotonergic receptors and are therefore useful in the treatment of certain psychic and neurologic disorders.

14 Claims, No Drawings

4-ARYL-1-(INDANMETHYL DIHYDROBENZOFURANMETHYL OR DIHYDROBENZOTHIOPHENEMETHYL) PIPERIDINES TETRAHYDROPYRIDINES OR PIPERAZINES

This is a continuation of application Ser. No. 08/999,868, filed Dec. 9, 1996, issued as U.S. Pat. No. 6,218,394, which is a continuation of International Application No. PCT/DK95/00230, filed Jun. 8, 1995. Each of these prior applications is hereby incorporated herein by reference, in its entirety.

FIELD OF THE INVENTION

The present invention relates to a novel class of 4-aryl-1-(indanmethyl, dihydrobenzofuranmethyl or dihydrobenzothiophenemethyl)piperidine, -tetrahydropyridine or -piperazine compounds having effects at central serotonergic receptors. These methylamine compounds are therefore useful in the treatment of certain psychic and neurologic disorders.

BACKGROUND OF THE INVENTION

A few aminomethylindan, -dihydrobenzofurane and -dihydrobenzothiophene compounds are known from the prior art.

So, EP patent 0 281 261 discloses 1-aminomethylindan, 3-aminomethylbenzofurane and 3-aminomthylbenzo-thiophene derivatives with a hydroxy group or a substituted hydroxy group in the 6-position (indan) or 5-position (benzofurane, benzothiophene). These compounds were found to show central dopamine agonist activity, in particular to show effect at presynaptic dopamine receptors.

In U.S. Pat. No. 4,500,543 certain 1-aminomethyl-phtalane compounds are said to show adrenergic effects and, accordingly, antihypertensive and heart rate decreasing properties. Said patent generically covers compounds having substituents in the 5-, 6- and/or 7-position.

EP 0325963 A1 discloses among other compounds a class of 1-aminomethyl indan compounds in which the aminomethyl group may constitute a 1-pyrrolylmethyl group which is substituted with thienyl or phenyl. The compounds are claimed to be $\alpha_2$ antagonists useful in the treatment of depression, metabolic disorders, glaucoma, migraine and hypertension.

Furthermore, EP 0490772 A1 describes i.a. a class of 4-benzofuranyl- or 4-benzodioxanyl-1-indanylmethyl piperazine compounds being 5-$HT_{1A}$ ligands.

EP 0428437 generically covers a very broad class of 1,2-benzoisoxazole compounds including certain 3-[1-[(1-indanyl)methyl]-1,2-benzoisoxazoles. However, only one such compound is examplified and in that case without giving any data. The compounds are said to show dopamine and serotonin antagonistic activities.

U.S. Pat. No. 3,886,168 relates to 1-[(indan-1-yl)methyl] piperidine compounds having antihypertensive activity.

Various effects are known with respect to compounds which are ligands at the different serotonin receptor subtypes. As regards the 5-$HT_{2A}$ receptor, which was previously referred to as the 5-$HT_2$ receptor, the following effects have e.g. been reported:

The 5-$HT_{2A}$ antagonist ritanserin (Meert, T. F.; Janssen, P. A. J. *Drug. Dev. Res.* 1989, 18, 119.) has been shown to be effective in the treatment of anxiety and depression presumably through improvement of the sleep quality. Furthermore, selective, centrally acting 5-$HT_{2A}$ antagonists have been shown to have an effect towards the negative symptoms of schizophrenia and to reduce extrapyramidal side-effects caused by treatment with classical neuroleptics in schizophrenic patients (Gelders, Y. G., British J. Psychiatry, 1989, 155 (suppl.5), 33). Finally, selective 5-$HT_{2A}$ antagonists could be effective in the prophylaxis and treatment of migraine since it is known that 5-HT is involved in migraine attacks. The links between 5-HT and migraine attacks are several and they suggest a number of mechanisms whereby 5-HT may be involved (Scrip Report; "Migraine—Current trends in research and treatment"; PJB Publications Ltd.; May 1991).

The serotonin 5-$HT_{2A}$ antagonist, MDL 100,907 (Sorensen, S. M. et al., *J. Pharmacol. Exp. Ther.* 1993, 266, 684–691), and certain compounds within series of 1-phenylindoles (WO 93/12790) and 3-phenylindole derivatives (WO 93/14758) have shown anti-psychotic activity in animal models with indication of no liability of no liability to cause extrapyramidal side effects (EPS).

Clinical studies of known 5-$HT_{1A}$ partial agonists such as e.g. buspirone, 8-[4-[4-(2-pyrimidyl)-1-piperazinyl]butyl]-8-azaspiro[4,5]decane-7,9-dione, gepirone, 4,4-dimethyl-1-[4-[4-(2-pyrimidyl)-1-piperazinyl]butyl]-2,6-piperidinedione, and ipsapirone, 2-[4-[4-(2-pyrimidyl)-1-piperazinyl]butyl]-1,2-benzothiazol-3(2H)-one-1,1-dioxide, have shown that 5-$HT_{1A}$ partial agonists are useful in the treatment of anxiety disorders such as generalised anxiety disorder, panic disorder, and obsessive compulsive disorder (Glitz, D. A., Pohl, R., *Drugs* 1991, 41, 11). Preclinical studies indicate that also full agonists are useful in the treatment of the above mentioned anxiety related disorders (Schipper, *Human Psychopharmacol.*, 1991, 6, S53).

There is also evidence, both clinical and preclinical, in support of the beneficial effect of 5-$HT_{1A}$ partial agonists in the treatment of depression, impulse control disorders and alcohol abuse (van Hest, *Psychopharmacol.*, 1992, 107, 474; Schipper et al, *Human Psychopharmacol.*, 1991, 6, S53; Cervo et al, *Eur. J. Pharm.*, 1988, 158, 53; Glitz and Poh, *Drugs* 1991, 41, 11; Grof et al., *Int. Clin. Psychopharmacol.* 1993, 8, 167–172; Ansseau et al., *Human Psychopharmacol.* 1993, 8, 279–283).

5-$HT_{1A}$ agonists and partial agonists inhibit isolation-induced aggression in male mice indicating that these compounds are useful in the treatment of aggression (Sanchéz et al., *Psychopharmacology*, 1993, 110, 53–59).

Furthermore, 5-$HT_{1A}$ ligands have been reported to show antipsychotic effect in animal models (Wadenberg and Ahlenius, *J. Neural. Transm.*, 1991, 83, 43; Ahlenius, *Pharmacol.&Toxicol.*, 1989, 64, 3; Lowe et al., *J. Med. Chem.*, 1991, 34, 1860; New et al., *J. Med. Chem.*, 1989, 32, 1147; and Martin et al., *J. Med. Chem.*, 1989, 32, 1052).

Recent studies also indicate that 5-$HT_{1A}$ receptors are important in the serotonergic modulation of haloperidol-induced catalepsy (Hicks, *Life Science* 1990, 47, 1609, Wadenberg et al. *Pharmacol.Biochem. & Behav.* 1994, 47, 509–513) suggesting that 5-$HT_{1A}$ agonists are useful in the treatment of EPS induced by conventional antipsychotic agents such as haloperidol.

5-$HT_{1A}$ agonists have shown neuroprotective properties in rodent models of focal and global cerebral ischaemia and may, therefore, be useful in the treatment of ischaemic disease states (Prehn, *Eur. J. Pharm.* 1991, 203, 213).

Pharmacological studies have been presented which indicates that 5-$HT_{1A}$ antagonists are useful in the treatment of senile dementia (Bowen et al, *Trends Neur. Sci.* 1992, 15, 84).

Both in animal models and in clinical trials it has been shown that 5-$HT_{1A}$ agonists exert antihypertensive effects via a central mechanism (Saxena and Villalón, *Trends Pharm. Sci.* 1990, 11, 95; Gillis et al, *J. Pharm. Exp. Ther.* 1989, 248, 851). 5-$HT_{1A}$ ligands may, therefore, be beneficial in the treatment of cardiovascular disorders.

5-HT reuptake inhibitors are well known antidepressant drugs.

As 5-$HT_{1A}$ and 5-$HT_{2A}$ receptor ligand classes of compounds and 5-HT reuptake inhibitors have different activities in different animal models predictive of anxiolytic and antiaggressive effects (Perregaard et al., Recent Developments in Anxiolytic. *Current Opinion in Therapeutic Patents* 1993, 1, 101–128) and/or in models predictive of effects in other psychic disorders it might also be highly beneficial to treat complex states of anxiety, depression, or other psychic disorders with a drug which have combined serotonergic effects.

SUMMARY OF THE INVENTION

It has now been found that certain novel 4-aryl-1-(indanmethyl, dihydrobenzofuranmethyl or dihydrobenzothiophenemethyl)piperidines, -tetrahydropyridines or -piperazines interact potently with central serotonergic receptors, in particular with the 5-$HT_{1A}$ and/or the 5-$HT_{2A}$ receptors.

Accordingly, the present invention relates to novel compounds of the formula I.

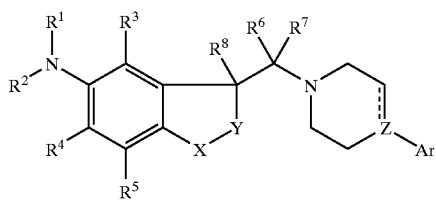

wherein one of X and Y is $CH_2$ and the other one is selected from the group consisting of $CH_2$, O, and S;

the dotted line, emanating from Z, indicates an optional bond; when it does not indicate a bond Z is N, CH or COH; and when it indicates a bond Z is C;

Ar is phenyl, 2-thienyl, 3-thienyl, 2-furanyl, 3-furanyl, 2-pyrimidyl, 1-indolyl, 2-indolyl, 3-indolyl, 1-indol-2-onyl, 3-indol-2-onyl, 2- or 3-benzofuranyl, 2- or 3-benzothiophenyl, 1-naphthyl or 2-naphthyl, each optionally substituted with halogen, lower alkyl, lower alkoxy, lower alkylthio, hydroxy, lower alkylsulfonyl, cyano, trifluoromethyl, trifluromethylsulfonyloxy, cycloalkyl, cycloalkyl-lower-alkyl, nitro, amino, lower alkylamino, di-lower alkylamino, acylamino or $C_{1-2}$ alkylenedioxy;

$R^1$ is hydrogen, lower alkyl, lower alkenyl, lower alkynyl, cycloalk(en)yl, cycloalk(en)-yl-lower alk(en/yn)yl, aryl, aryl-lower alkyl, acyl, thioacyl, lower alkylsulfonyl, trifluoromethylsulfonyl, arylsulfonyl, $R^1$ is a group $R^9$VCO— where V is O or S and $R^9$ is lower alkyl, cycloalkyl, cycloalkyl-lower-alkyl or aryl, or $R^1$ is a group $R^{10}R^{11}$NCO— or $R^{10}R^{11}$NCS— wherein $R^{10}$ and $R^{11}$ are independently hydrogen, lower alkyl, cycloalkyl, cycloalkyl-lower-alkyl or aryl, or $R^{10}$ and $R^{11}$ together with the N-atom to which they are linked, form a pyrrolidinyl, piperidinyl or perhydroazepin group;

$R^2$ is hydrogen, lower alkyl, cycloalkyl or cycloalkyl-lower-alkyl;

or $R^1$ and $R^2$ together with the N-atom to which they are linked form a group,

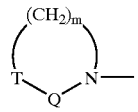

wherein Q is C=O, C=S or $CH_2$; T is NH, S, O or $CH_2$; and m is 1–4, inclusive;

$R^3$–$R^5$ are independently hydrogen, halogen, lower alkyl, lower alkylcarbonyl, phenylcarbonyl, halogen substituted phenylcarbonyl, lower alkoxy, lower alkylthio, hydroxy, lower alkylsulfonyl, cyano, trifluoromethyl, cycloalkyl, cycloalkyl-lower-alkyl or nitro;

$R^6$ and $R^7$ are each hydrogen or lower alkyl or they are linked together to constitute a 3–7-membered carbocyclic ring;

$R^8$ is hydrogen or lower alkyl;

any alkyl, cycloalkyl or cycloalkylalkyl group present being optionally substituted with one or two hydroxy groups, which again are optionally esterified with an aliphatic or aromatic carboxylic acid; and any aryl substituent present being optionally substituted with halogen, lower alkyl, lower alkoxy, lower alkylthio, hydroxy, lower alkylsulfonyl, cyano, trifluoromethyl, trifluoromethylsulfonyloxy, cycloalkyl, cycloalkyl-lower-alkyl or nitro;

and pharmaceutically acceptable acid addition salts thereof.

The compounds of the invention have been found to show potent affinity to 5-$HT_{1A}$ receptors and/or to 5-$HT_{2A}$ receptors. In addition to the effect at these receptor subtypes, certain of the present compounds also show 5-HT reuptake inhibiting effect.

Accordingly, the compounds of the invention are considered useful in the treatment of positive and negative symptoms of schizophrenia, other psychoses, anxiety disorders, such as generalised anxiety disorder, panic disorder, and obsessive compulsive disorder, depression, alcohol abuse, impulse control disorders, aggression, side effects induced by conventional antipsychotic agents, ischaemic disease states, migraine, senile dementia and cardiovascular disorders and in the improvement of sleep.

In another aspect the invention provides a pharmaceutical composition comprising at least one compound of Formula I as defined above or a pharmaceutically acceptable acid addition salt thereof or prodrug thereof in a therapeutically effective amount and in combination with one or more pharmaceutically acceptable carriers or diluents.

In a further aspect the present invention provides the use of a compound of Formula I as defined above or an acid addition salt or prodrug thereof for the manufacture of a pharmaceutical preparation for the treatment of the above mentioned disorders.

DETAILED DESCRIPTION OF THE INVENTION

Compounds of general Formula I exist as optical isomers thereof and such optical isomers are also embraced by the invention.

Prodrugs of the compounds of general Formula I are also embraced by the invention.

The term cycloalkyl designates a carbocyclic ring having 3–8 carbon atoms, inclusive, or a bicyclic or tricyclic carbocycle, such as adamantyl.

The term lower alkyl refers to a branched or unbranched alkyl group having from one to six carbon atoms inclusive, such as methyl, ethyl, 1-propyl, 2-propyl, 1-butyl, 2-butyl, 2-methyl-2-propyl and 2-methyl-1-propyl. The terms lower alkoxy, lower alkylthio, lower alkylsulfonyl, lower alkylamino, lower alkylcarbonyl, etc. designate such groups in which the alkyl group is lower alkyl as defined above. Similarly, lower alkenyl and alkynyl, respectively, designate such groups having from two to six carbon atoms, inclusive. Preferred groups are those having up to four carbon atoms.

The term aryl refers to a mono- or bicyclic carbocyclic or heterocyclic aromatic group, such as phenyl, indolyl, thienyl, pyrimidyl, oxazolyl, isoxazolyl, thiazolyl, isothiazolyl, imidazolyl, benzofuranyl, benzothienyl, pyridyl, naphthyl and furanyl, in particular phenyl, pyrimidyl, indolyl, and thienyl.

Halogen means fluoro, chloro, bromo or iodo.

As used herein the term acyl refers to a formyl, lower alk(en/yn)ylcarbonyl, arylcarbonyl, aryl-lower alk(en/yn)ylcarbonyl, cycloalkylcarbonyl, or cycloalkyl-lower-alk(en/yn)ylcarbonyl group.

The term thioacyl is the corresponding acyl group in which the carbonyl group is replaced with a thiocarbonyl group.

The expression alk(en/yn)yl means that the group may be an alkyl, alkenyl, or alkynyl group.

In Formula I, X is preferably $CH_2$ or S and Y is preferably $CH_2$ and most preferably they are both $CH_2$.

$R^1$ is preferably acyl, lower alkyl, lower alkoxy, a group $R^{10}R^{11}NCO—$ or $R^{10}R^{11}NCS—$ wherein $R^{10}$ is hydrogen, lower alkyl, cycloalkyl, cycloalkyl-lower-alkyl or aryl and $R^{11}$ is hydrogen or lower alkyl or $R^{10}$ and $R^{11}$ together with the N-atom to which they are linked, form a pyrrolidinyl, piperidinyl or perhydroazepin group. Most preferably, $R^1$ is formyl, acetyl, methylaminocarbonyl, methylaminothiocarbonyl, dimethylaminocarbonyl, dimethylaminothiocarbonyl, methylsulfonyl, aminocarbonyl, cyclopropylcarbonyl, methyl, pyrrolidinyl-carbonyl or 4-fluorophenylaminocarbonyl. $R^2$ is preferably hydrogen or lower alkyl, most preferably hydrogen or methyl, or $R^1$ and $R^2$ are linked together to form a 5–7 membered unsubstituted lactam ring or a pyrrolidinyl, piperidinyl or perhydroazepin.

$R^3$–$R^5$ are preferably hydrogen, fluoro, chloro, bromo, methyl, trifluoromethyl or acetyl and $R^6$–$R^8$ are preferably all hydrogen.

Finally, Ar is preferably phenyl, 3-indolyl, 1-indolyl, or pyrimidyl or phenyl, 3-indolyl, 1-indolyl or pyrimidyl substituted with halogen.

A preferred subclass of compounds are those wherein $R^1$ is acetyl and $R^2$ is H and in particular such compounds wherein Ar is indolyl or phenyl substituted with halogen, especially chloro. If Ar is 3-indolyl it is preferably substituted in the 6-position and if it is phenyl, it is preferably substituted in the 4-position.

Another preferred subclass of compounds of the invention are those wherein $R^1$ is a group $R^{10}R^{11}NCO—$ or $R^{10}R^{11}NCS—$ wherein $R^{10}$ is hydrogen, lower alkyl, cycloalkyl, cycloalkyl-lower-alkyl or aryl and $R^{11}$ is hydrogen or lower alkyl and $R^2$ is hydrogen.

In a further preferred subclass of compounds $R^1$ is hydrogen, lower alkyl or lower alkylsulfonyl in particular methyl or methylsulfonyl and $R^2$ is hydrogen or lower alkyl, in particular methyl, or $R^1$ and $R^2$ are linked together to form a pyrrolidinon ring or a pyrrolidinyl ring.

Preferred compounds are:
1-(6-Acetylaminoindan-1-ylmethyl)-4-(4-fluorophenyl)piperidine.
(+)-1-(6-Acetylaminoindan-1-ylmethyl)-4-(4-fluorophenyl)piperidine.
(−)-1-(6-Acetylaminoindan-1-ylmethyl)-4-(4-fluorophenyl)piperidine
1-(6-Acetylamino-5-fluoroindan-1-ylmethyl)-4-(4-fluorophenyl)piperidine.
1-(6-Acetylamino-4-fluoroindan-1-ylmethyl)-4-(4-fluorophenyl)piperidine.
1-(6-Acetylamino-4-bromoindan-1-ylmethyl)-4-(4-fluorophenyl)piperidine.
1-(6-Acetylamino-4-nitroindan-1-ylmethyl)-4-(4-fluorophenyl)piperidine.
1-(6-Acetylamino-4-cyanoindan-1-ylmethyl)-4-(4-fluorophenyl)piperidine.
1-(6-Acetylamino-5-chloroindan-1-ylmethyl)-4-(4-fluorophenyl)piperidine.
1-(6-Acetylamino-5-bromoindan-1-ylmethyl)-4-(4-fluorophenyl)piperidine.
1-(6-Acetylamino-5-cyanoindan-1-ylmethyl)-4-(4-fluorophenyl)piperidine.
1-(6-Acetylamino-7-chloroindan-1-ylmethyl)-4-(4-fluorophenyl)piperidine.
1-(6-Acetylamino-7-fluoroindan-1-ylmethyl)-4-(4-fluorophenyl)piperidine.
1-(5-Acetyl-6-acetylaminoindan-1-ylmethyl)-4-(4-fluorophenyl)piperidine.
1-(6-Acetylamino-1-methylindan-1-ylmethyl)-4-(4-fluorophenyl)piperidine.
1-(6-Acetylaminoindan-1-ylmethyl)-4-(3-fluorophenyl)piperidine.
1-(6-Acetylaminoindan-1-ylmethyl)-4-(2-fluorophenyl)piperidine.
1-(6-Acetylaminoindan-1-ylmethyl)-4-(4-methylphenyl)piperidine.
1-(6-Acetylaminoindan-1-ylmethyl)-4-(4-dimethylaminophenyl)piperidine.
1-(6-Acetylaminoindan-1-ylmethyl)-4-(4-aminophenyl)piperidine.
1-(6-Acetylaminoindan-1-ylmethyl)-4-(3-trifluoromethylphenyl)piperidine.
1-(6-Acetylaminoindan-1-ylmethyl)-4-(4-fluorophenyl)piperidine.
1-(5-Acetylamino-2,3-dihydrobenzothiophen-3-ylmethyl)-4-(4-fluorophenyl)piperidine.
1-(6-Acetylamino-1,3-dihydroisobenzofuran-1-ylmethyl)-4-(4-fluorophenyl)piperidine.
1-(6-Acetylaminoindan-1-ylmethyl)-4-(4-chlorophenyl)piperazine.
1-(6-Acetylaminoindan-1-ylmethyl)-4-(3-chlorophenyl)piperazine.
1-(6-Acetylaminoindan-1-ylmethyl)-4-(2-chlorophenyl)piperazine.
1-(6-Acetylaminoindan-1-ylmethyl)-4-(4-trifluoromethylsulfonyloxyphenyl)piperazine.
1-(6-Acetylaminoindan-1-ylmethyl)-4-(3,4-dichlorophenyl)piperazine.
1-(6-Acetylaminoindan-1-ylmethyl)-4-(3,4-dichlorophenyl)piperidine.
1-(6-Acetylaminoindan-1-ylmethyl)-4-(2-methoxyphenyl)piperazine.
1-(6-Acetylaminoindan-1-ylmethyl)-4-(4-fluorophenyl)-1,2,3,6-tetrahydropyridine.

1-(6-Acetylaminoindan-1-ylmethyl)-4-(4-chlorophenyl)-1,2,3,6-tetrahydropyridine.
1-(6-Acetylaminoindan-1-ylmethyl)-4-(2-pyrimidyl)piperidine.
1-(6-Acetylaminoindan-1-ylmethyl)-4-(2-pyrimidyl)piperazine.
1-(6-Acetylaminoindan-1-ylmethyl)-4-(2-pyridinyl)piperazine.
1-(6-Acetylaminoindan-1-ylmethyl)-4-(3-thienyl)piperidine.
1-(6-Acetylaminoindan-1-ylmethyl)-4-(2-thienyl)piperidine.
1-(6-Acetylaminoindan-1-ylmethyl)-4-(3-thienyl)piperazine.
1-(6-Acetylaminoindan-1-ylmethyl)-4-(1-naphthyl)piperidine.
1-(6-Acetylaminoindan-1-ylmethyl)-4-(2-naphthyl)piperidine.
1-(6-butanoylaminoindan-1-ylmethyl)-4-(4-fluorophenyl)piperidine
1-(6-Formylaminoindan-1-ylmethyl)-4-(4-fluorophenyl)piperidine.
1-(6-Formylaminoindan-1-ylmethyl)-4-(4-fluorophenyl)piperazine.
4-(4-Fluorophenyl)-1-(6-methansulfonylaminoindan-1-ylmethyl)piperidine.
1-(6-Cyclopropylcarbonylaminoindan-1-ylmethyl)-4-(4-fluorophenyl)piperidine.
1-(6-Cyclopentylcarbonylaminoindan-1-ylmethyl)-4-(4-fluorophenyl)piperidine.
4-(4-Fluorophenyl)-1-(6-methylaminocarbonylaminoindan-1-ylmethyl)piperidine.
1-[6-(4-Fluorophenyl)aminocarbonylaminoindan-1-ylmethyl]-4-(4-fluorophenyl)piperidine.
4-(4-Fluorophenyl)-1-(6-methylaminothiocarbonylaminoindan-1-ylmethyl)piperidine.
1-(6-Dimethylaminocarbonylaminoindan-1-ylmethyl)-4-(4-fluorophenyl)piperidine.
1-(6-Dimethylaminothiocarbonylaminoindan-1-ylmethyl)-4-(4-fluorophenyl)piperidine.
4-(4-Fluorophenyl)-1-[6-(1-pyrrolidinyl)carbonylaminoindan-1-ylmethyl]piperidine.
1-(6-Aminocarbonylaminoindan-1-ylmethyl)-4-(4-fluorophenyl)piperidine.
1-(6-Ethoxycarbonylaminoindan-1-ylmethyl)-4-(4-fluorophenyl)piperidine.
1-[6-(N,N-dimethylamino)indan-1-ylmethyl]-4-(4-fluorophenyl)piperidine.
3-[1-(5-Acetylamino-2,3-dihydrobenzothiophen-3-ylmethyl)piperidin-4-yl]-5-chloro-1H-indole.
3-[1-(5-Acetylamino-2,3-dihydrobenzothiophen-3-ylmethyl)-1,2,3,6-tetrahydropyridin-4-yl]-5-chloro-1H-indole.
3-[1-(6-Acetylaminoindan-1-ylmethyl)piperidin-4-yl]-5-fluoro-1H-indole.
3-[1-(6-Acetylamino-2,3-dihydrobenzothiophen-3-ylmethyl)-1,2,3,6-tetrahydropyridin-4-yl]-5-fluoro-1H-indole.
3-[1-(6-Acetylaminoindan-1-ylmethyl)-1,2,3,6-tetrahydropyridin-4-yl]-6-chloro-1H-indole.
3-[1-(6-Acetylaminoindan-1-ylmethyl)piperidin-4-yl]-6-chloro-1H-indole.
3-[1-(6-Acetylaminoindan-1-ylmethyl)piperidin-4-yl]-6-chloro-1-methyl-1H-indole.
1-[1-(6-Acetylaminoindan-1-ylmethyl)piperidin-4-yl]-6-chloro-1H-indole.
1-[1-(6-Acetylaminoindan-1-ylmethyl)piperidin-4-yl]-5-chloro-1H-indole.
3-[1-(6-Acetylaminoindan-1-ylmethyl)-1,2,3,6-tetrahydropyridin-4-yl]-5-chloro-1H-indole.
4-(4-Fluorophenyl)-1-[6-(1-pyrrolidin-2-onyl)indan-1-ylmethyl]piperidine.
4-(4-Fluorophenyl)-1-[6-(1-piperidin-2-onyl)indan-1-ylmethyl]piperidine.
1-[6-(4-Fluorophenylamino)indan-1-ylmethyl]-4-(4-fluorophenyl)piperidine
3-[1-(6-Acetylaminoindan-1-ylmethyl)piperidin-4-yl]-6-chlorobenzothiophene.
3-[1-(6-Acetylaminoindan-1-ylmethyl)-1,2,3,6-tetrahydropyridin4-yl]-6-chlorobenzothiophene.
3-[1-(6-Acetylaminoindan-1-ylmethyl)piperidin-4-yl]-5-chlorobenzothiophene.
2-[1-(6-Acetylaminoindan-1-ylmethyl)piperidin-4-yl]-6-chlorobenzothiophene.
3-[1-(6-Acetylaminoindan-1-ylmethyl)piperidin-4-yl]-6-chlorobenzofurane.
3-[1-(6-Acetylaminoindan-1-ylmethyl)piperidin-4-yl]-6-chloro-1H-indol-2-one
3-[1-(6-Acetylaminoindan-1-ylmethyl)piperidin-4-yl]-6-chloro-1-methyl-1H-indol-2-one.
3-[1-(6-Acetylaminoindan-1-ylmethyl)-1,2,3,6-tetrahydropyridin-4-yl]-6-chloro-1-methyl-1H-indol-2-one.
2-[1-(6-Acetylaminoindan-1-ylmethyl)piperidin-4-yl]-6-chloro-1H-indole.
1-[1-(6-Acetylaminoindan-1-ylmethyl)piperidin-4-yl]-5-chloro-1H-indol-2-one.
3-[1-(6-Methylaminokarbonylaminoindan-1-ylmethyl)piperidin-4-yl]-5-chloro-1H-indole.
3-[1-(6-Methylaminokarbonylaminoindan-1-ylmethyl)-1,2,3,6-tetrahydropyridin-4-yl]-6-chloro-1H-indole.
1-(6-Acetylaminoindan-1-ylmethyl)-4-(4-bromophenyl)piperidine.
1-(6-Acetylaminoindan-1-ylmethyl)-4-hydroxy-4-(4-chlorophenyl)piperidine.
1-(6-Acetylaminoindan-1-ylmethyl)-4-(3-trifluoromethyl-4-chlorophenyl)piperazine.
1-(6-Acetylaminoindan-1-ylmethyl)-4-(2-chloro-3-thienyl)piperazine.
1-(6-Acetylaminoindan-1-ylmethyl)-4-(4-chloro-2-thienyl)piperidine.
1-(6-Acetylaminoindan-1-ylmethyl)-4-(3,4-methylendioxyphenyl)piperidine.
1-(6-Acetylaminoindan-1-ylmethyl)-4-(3,4-methylendioxyphenyl)piperazine.
1-(6-Methylaminocarbonylaminoindan-1-ylmethyl)-4-(3,4-methylendioxyphenyl)piperazine.
1-(6-Acetylaminoindan-1-ylmethyl)-4-hydroxy-4-(3-trifluoromethyl-4-chlorophenyl)piperidine.
1-(6-Acetylaminoindan-1-ylmethyl)-4-acetyloxy-4-(3-trifluoromethyl-4-chlorophenyl)piperidine.
5-chloro-1-[1-(6-methylaminocarbonylaminoindan-1-ylmethyl)piperidin-4-yl]-1H-indole The acid addition salts of the invention are pharmaceutically acceptable salts of the compounds of Formula I formed with non-toxic acids. Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of such inorganic salts are those with hydrochloric, hydrobromic, sulfuric, sulfamic, phosphoric, and nitric acids.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients, or other additives normally used in the art may be used.

Conveniently, the compounds of the invention are administered in unit dosage form containing said compounds in an amount of about 0.01 to 100 mg.

The total daily dose is usually in the range of about 0.05–500 mg, and most preferably about 0.1 to 50 mg of the active compound of the invention.

The invention moreover relates to a method for the preparation of the novel 4-Aryl-1-[amino(indan, dihydrobenzofuran or dihydrobenzothiophene)methyl] piperidines, -tetrahydropyridines or -piperazines of Formula I, comprising:

a) reacting an amino derivative of the following Formula II:

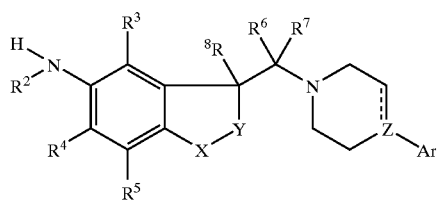

II wherein $R^2$–$R^8$, X, Y, Z, Ar, and the dotted line are as previously defined, with a reagent of the formula $R^{1'}$-hal or $R^{1'}$-OCOR, in which formulas hal is halogen, R is alkyl, aryl or alkoxy and $R^{1'}$ is acyl, thioacyl, a group $R^9VCO—$, or a group $R^{10}R^{11}NCO—$ or $R^{10}R^{11}NCS—$ where $R^9$, V, $R^{10}$ and $R^{11}$ are as previously defined except that neither $R^{10}$ nor $R^{11}$ may be hydrogen, or with a lower alkylsulfonyl halogenide, trifluoromethylsulfonyl halogenide or an isocyanate or thioisocyanate of the formula $R^{10}—N=C=O$ or $R^{10}—N=C=S$ wherein $R^{10}$ is as previously defined;

b) in order to prepare a compound of Formula I wherein $R^1$ is lower alk(en/yl)yl, cycloalk(en)yl, cycloalk(en)yl-lower alk(en/yn)yl or aryl-lower alkyl, alkylating an amino derivative of Formula II with an alkylating agent such as an alkylhalogenide $R^1$-hal, a mesylate $R^{1''}OSO_2CH_3$, a tosylate $R^{1''}OSO_2C_6H_4—CH_3$, or a similar alkylating reagent with suitable leaving groups, $R^1$ being lower alkyl, lower alkenyl, lower alkynyl, cycloalk(en)yl, cycloalk(en)yl-lower alk(en/yn)yl or aryl-lower alkyl;

c) reducing the tetrahydropyridinyl double bond in derivatives of the following Formula III:

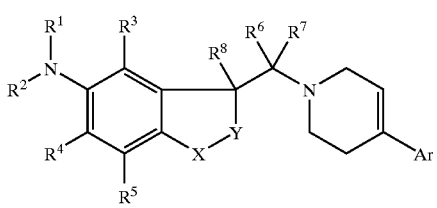

III wherein $R^1$–$R^8$, X, Y, and Ar are as previously defined; or d) alkylating an arylpiperazine, arylpiperidine, or aryltetrahydropyridine of the formula V with an alkylating derivative of the formula IV:

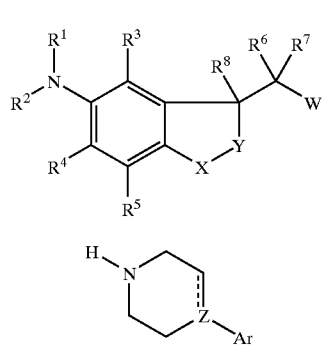

IV

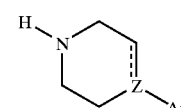

V wherein $R^1$–$R^8$, X, Y, Z, Ar, and the dotted line are as previously defined, and w is a leaving group such as eg. halogen, mesylate, or tosylate; or e) in order to obtain to form a compound of Formula I in which the substituents $R^1$ and $R^2$ together constitute a ring, ringclosure of a derivative of Formula VI:

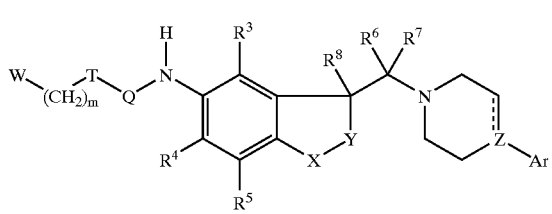

VI in which $R^3$–$R^8$, X, Y, Z, Ar, m, Q, T and the dotted line are as previously defined and w is a leaving group such as halogen, mesylate, or tosylate;

f) in order to obtain a compound of Formula I in which $R^1$ is lower alk(en/yn)yl, cycloalk(en)yl, cycloalk(en)yl-lower alk(en/yn)yl or aryl-lower alkyl, reducing the carbonyl group of an amide derivative of the following Formula VII:

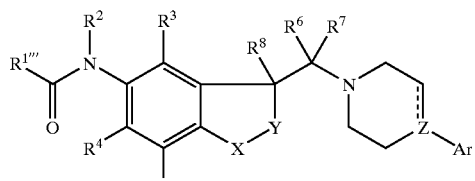

VII wherein $R^2$–$R^8$, X, Y, Z, Ar and the dotted line are as previously defined and $R^{1'''}$ is such a group that the group $R^{1'''}CH_2$ constitutes a lower alk(en/yn)yl, cycloalk(en)yl, cycloalk(en)yl-lower alk(en/yn)yl or aryl-lower alkyl as embraced by the definition of $R^1$; or g) introducing a substituent $R^3$, $R^4$ or $R^5$ by reacting a compound of the following Formula VIII:

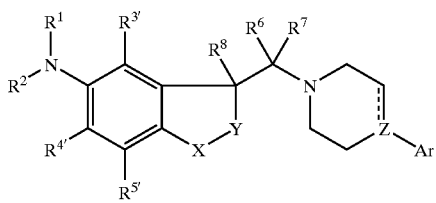

wherein one of $R^{3'}-R^{5'}$ is hydrogen and the other two are the corresponding $R^3$, $R^4$ or $R^5$ as previously defined and $R^1$, $R^2$, $R^6-R^8$, X, Y, Z, Ar and the dotted line are as previously defined, by using a reactive reagent such as a halogen or a halogenating agent, a sulfonating agent, a nitration agent or a reactive agent generating carbonium ions (RCO+, R+) wherein R is alkyl alkynyl, aryl cycloalkyl, or cycloalk (en/yn)yl; or h) reducing the double bond in a compound of the following Formula IX:

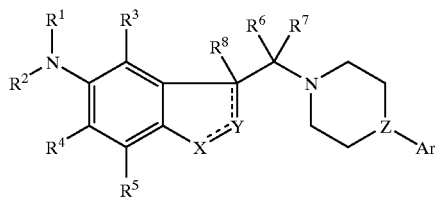

wherein $R^1-R^8$, X, Y, Z, and Ar are as previously defined and one of the two dotted lines indicates a double bond; or i) reducing the amide carbonyl in a compound of the following Formula X:

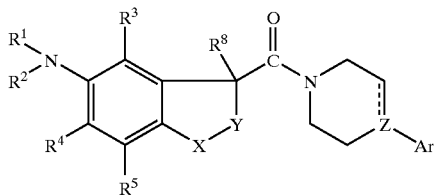

wherein $R^1-R^5$, $R^8$, X, Y, Z, Ar and the dotted line are as previously defined.

whereupon the compound of Formula I is isolated as the free base or a pharmaceutically acceptable acid addition salt thereof.

The reaction in Method a) is conveniently performed at low temperature (eg. below room temperature) in an inert solvent such as acetone, dichloromethane, tetrahydrofuran or dimethoxyethane when reactive carboxylic acid chlorides, isocyanates, or isothiocyanates are used. Formylated amines are prepared from the corresponding amines by reaction in formic acid, with esters of formic acid, or by reaction with mixed formic acid anhydride prepared in situ. Generally reaction temperatures are between 0° C. and the boiling point of the formyl precursor compounds.

The alkylations according to Methods b) and d) are generally performed by refluxing in a suitable solvent such as acetone, methyl isobutyl ketone, tetrahydrofuran, dioxane, ethanol or 2-propanol in the presence of a base such as triethylamine or potassium carbonate.

The reductions of double bonds according to Methods c) and h) are generally performed by catalytic hydrogenation at low pressure (<3 atm.) in a Parr apparatus, or by using reducing agents such as diborane in inert solvents such as tetrahydrofuran, dioxane, or diethyl ether.

The reductions according to Methods f) and i) are generally performed by use of $LiAlH_4$, $AlH_3$ or diborane in an inert solvent such as tetrahydrofuran, dioxane, or diethyl ether at room temperature or at a slightly elevated temperature.

The halogenation according to Method g) is generally performed by use of chlorine, bromine, or N-chlorosuccinimide, N-bromosuccinimide or another halogen precursor molecule, conveniently in the presence of a catalyst such as Fe ions or a mineral acid.

1-Unsubstituted 4-arylpiperazines of Formula V (Z=N) are either commercially available or may be synthesized from the corresponding anilines and N',N'-bis(2-chloroethyl)amine by refluxing in high boiling solvents as chlorobenzene typically for 2–3 days according to methods described by Martin et al. *J.Med.Chem.* 1989, 32 1052–1056.

4-Arylpiperidines of formula V (Z=CH) are either commercially available or prepared as described in eg. U.S. Pat. No. 2,891,066; McElvain et al. J. Amer. Chem. Soc. 1950, 72, 3134; Bally et al *Chem.Ber.* 1887, 20, 2590. The corresponding 4-aryl-1,2,3,6-tetrahydropyridines of Formula V (Z=C) are prepared from N-protected 4-piperidones by addition of properly substituted aryl lithium or magnesium halides followed by acid catalyzed water elimination. The N-protecting group (carbamate, benzyl, sulfonyl, acetyl) is finally removed in a conventional manner.

Synthesis of 3-(4-piperidinyl)-1H-indoles and 3-(1,2,3,6-tetrahydropyridin-4-yl)-1H-indoles is described in the Experimental Section.

Key intermediates such as 1-indancarboxylic acid (V. Asham and W. H. Linnell, *J. Chem. Soc.* 1954, 4691–4693, Hansen et al. *Helv.Chim.Acta* 1982, 33, 325–343), and 5-nitro-3-benzothiophenecarboxylic acid (EP Pat. Appln. No. 88-301073 CA(110(9):75302y (1988) and references cited therein) were prepared according to well-known literature procedures.

EXPERIMENTAL SECTION

In the following the invention is further illustrated examples which, however, may not be construed as limiting.

In all the Examples, melting points were determined on a Büchi SMP-20 apparatus. Melting points are given as uncorrected values. $^1H$ NMR spectra were recorded at 250 MHz on a Bruker AC 250 spectrometer. Deuterated chloroform (99.8%D) or dimethylsulfoxide (99.9%D) were used as solvents. TMS was used as internal reference standard. Chemical shift values are expressed in ppm-values. The following abbreviations are used for multiplicity of NMR signals: s=singlet, d=doublet, t=triplet, q=quartet, qui= quintet, h=heptet, dd=double doublet, dt=double triplet, dq=double quartet, tt=triplet of triplets, m=multiplet.

EXAMPLE 1

6-Nitro-1-indancarboxylic acid, 1a

A solution of 1-indancarboxylic acid (30 g), prepared according to the method of Hansen et al. *Helv.Chim.Acta* 1982, 33, 325–343, in dichloromethane (50 ml) was mixed with concentrated sulphuric acid (300 ml) at −10° C. A mixture of 100% $HNO_3$ (11.4 g) in concentrated $H_2SO_4$ (96 ml) was added dropwise under vigorous stirring below −10° C. After stirring for one hour at 10° C., the mixture was poured onto ice. Extraction with ethyl acetate (2×300 ml), drying (anh. $MgSO_4$) and finally evaporation of the organic solvent afforded 42 g of the title compound. Mp: 126–130° C.

5-Nitro-3-benzothiophencarboxylic acid was prepared from 3-bromo-5-nitrobenzothiophene via the corresponding 3-cyanobenzothiophene derivative according to EP Pat. No. 88-301073 (CA110(9):75203y (1988), *J.Amer.Chem.Soc.* 1948, 70, 1955, and *J.Chem.Soc.(c)* 1967, 1899.

EXAMPLE 2

(Method 1)

1-Aminoindan-1-ylmethyl)-4-(4-fluorophenyl) piperidine, 2a

Dimethylformamide (DMF, 1 ml) was added to a solution of 6-nitro-1-indancarboxylic acid, 1a (13 g) and thionylchloride (18 ml) in dichloromethane (125 ml). The mixture was heated to reflux for 4 hours. Toluene was added and volatile material was evaporated in vacuo. The thus obtained carboxylic acid chloride was dissolved in dichloromethane (100 ml) and added dropwise to a solution of 4-(4-fluoro phenyl) piperidine (19.5 g) and triethylamine (7 ml) in dichloromethane (100 ml) at 0–5° C. The mixture was stirred at room temperature for another 1.5 hours. Water was added, the organic phase separated, washed with brine, dried (anh. $MgSO_4$), filtered, and dichloromethane evaporated in vacuo leaving the crude 6-nitroindan-1-carboxamide derivative as an oil (35 g). Purification by column chromatography on silica gel (eluted with a 1:1 mixture of ethyl acetate and heptane) yielded 12 g of the pure carboxamide as an oil. All of this oil was dissolved in refluxing 90% ethanol (350 ml). Fe-powder (10 g) and concentrated aqueous HCl (1 ml) were added successively in small portions during 10 minutes. The resulting mixture was refluxed for another 2.5 hours. Inorganic salts were filtered off while still hot and ethanol evaporated in vacuo. Diluted aqueous $NH_4OH$ was added until pH>9. Extraction with ethyl acetate (2×200 ml) and working-up as above of the organic phase afforded 8 g of the 6-aminoindan-1-carboxamide derivative. Mp: 144–145° C. To a suspension of $LiAlH_4$ (2.7 g) in dry tetrahydrofuran (THF, 125 ml) was added dropwise a solution of all of the carboxamide in THF (125 ml). The mixture was gently refluxed for 2 hours. After cooling to 10° C. water (10 ml) and a 15% aqueous NaOH solution were cautiously added to destroy excess LiAlH. Inorganic salts were filtered off and washed extensively with THF. The combined THF solutions were evaporated leaving 6.5 g of the title compound 2a as an oil. The hydrochloride salt crystallized from 2-propanol. Mp: 198–201° C. $^1$H NMR (DMSO-$d_6$): δ 1.85–2.40 (m, 6H); 2.60–2.90 (m, 3H); 3.00–3.15 (m, 3H); 3.35 (broad s, 3H); 3.45–3.60 (m, 2H); 3.65–3.75 (m, 1H); 6.45 (d, 1H); 6.50 (s, 1H); 6.95 (d, 1H); 7.15 (t, 2H); 7.25–7.35 (m, 2H).

In a similar manner the following aniline derivatives were prepared:

1-(6-Aminoindan-1-ylmethyl)-4-(2-methoxyphenyl) piperazine, 2b as an oil 1-(6-Aminoindan-1-ylmethyl)-4-(2-chlorophenyl) piperazine, 2c as an oil.

1-(6-Aminoindan-1-ylmethyl)-4-(3-chlorophenyl) piperazine, 2d as an oil.

1-(6-Aminoindan-1-ylmethyl)-4-(4-chlorophenyl) piperazine, 2e, mp: 98–109° C.

1-(5-Amino-2,3-dihydrobenzothiophen-3-ylmethyl)-4-(4-fluorophenyl)piperidine, 2f as an oil.

1-(6-Aminoindan-1-ylmethyl)-4-(4-fluorophenyl)-1,2,3,6-tetrahydropyridine, 2g, mp: 78–84° C.

1-(6-Aminoindan-1-ylmethyl)-4-(3,4-dichlorophenyl) piperazine, 2h, mp: 156–158° C. (washed with diethyl ether). $^1$H NMR (CDCl$_3$): δ 1.70–1.90 (m, 1H); 2.20–2.30 (m, 1H); 2.45 (dd, 1H); 2.55–2.75 (m, 6H); 2.75–2.90 (m, 2H); 3.20 (t, 4H); 3.20–3.35 (m, 1H); 3.55 (broad s, 2H); 6.50 (dd, 1H); 6.70–6.80 (m, 2H); 6.90–7.00 (m, 2H); 7.25 (d, 1H).

1-(6-Aminoindan-1-ylmethyl)-4-(3,4-methylendioxyphenyl)piperazine, 2i as an oil 1-(6-Aminoindan-1-ylmethyl)-4-hydroxy-4-(3-trifluoromethyl-4-chlorophenyl)-piperidine, 2i as an oil 1-(6-Aminoindan-1-ylmethyl)-4-(4-methylphenyl) piperidine, 2k as an oil.

1-(6-Aminoindan-1-ylmethyl)-4-(4-chlorophenyl)-1,2,3,6-tetrahydropyridine, 2l as an oil.

EXAMPLE 3

(Method i)

1-(6-Aminoindan-1-ylmethyl)-4-(4-fluorophenyl) piperazine, 3a

1-Indancarboxylic acid (20 g), DMF (2 ml), and thionylchloride (53 g) in dichloromethane (250) were refluxed for 4 hours. Volatile material was evaporated in vacuo and remaining thionylchloride was removed by evaporation with toluene in vacuo. The remaining carboxylic acid chloride was dissolved in dichloromethane (200 ml) and added dropwise to a solution of 1-(4-fluorophenyl)piperazine (58 g) in dichloromethane (200 ml) at 0–5° C. After stirring for 1.5 hours at room temperature, the organic phase was washed successively with water and brine and finally work-up as above of the organic phase yielded 66 g crude carboxamide. Purification by column chromatography on silica gel (eluted with ethyl acetate/heptane 1:1) yielded 36 g of crystalline product with mp: 119–124° C. All of this product was dissolved in concentrated $H_2SO_4$ (170 ml) at −10° C. A mixture of 100% $HNO_3$ (6.9 g) in concentrated $H_2SO_4$ (55 ml) was added dropwise under vigorous stirring below −10° C. The mixture was stirred for another hour at −5° C. The mixture was poured onto ice (500 g) and a 1:1 mixture of dichloromethane and ethyl acetate (300 ml) was added. The organic phase was separated and washed with diluted $Na_2CO_3$ solution (2×200 ml) and brine (200 ml). Work-up of the organic phase as above yielded 35 g of the crude 6-nitroindan-1-carboxamide derivative as an oil. The crude product was dissolved in 90% ethanol at reflux. Fe-powder (31.5 g) and concentrated aqueous HCl (3.1 ml) were added successively in small portions during 30 minutes. The resulting mixture was refluxed for another 2.5 hours. Inorganic salts were filtered off while still hot and ethanol evaporated in vacuo. Diluted aqueous $NH_4OH$ was added until pH≧9. Extraction with dichloromethane (2×200 ml) and working-up as above of the organic phase afforded 31 g of crystalline 6-aminoindan-1-carboxamide derivative. Mp: 143–149° C. To a suspension of LiAlH$_4$ (10.4 g) in dry THF (400 ml) was added dropwise a solution of all of the carboxamide in THF (400 ml). The mixture was gently refluxed for 2.5 hours. After cooling to 15° C. water (40 ml) and a 15% aqueous NaOH solution (10.4 ml) were cautiously added to destroy excess LiAlH$_4$. Inorganic salts were filtered off and washed extensively with THF. The combined THF solutions were evaporated leaving 23.7 g of the title compound 3a as an oil.

EXAMPLE 4

(Method a)

1-(6-Acetylaminoindan-1-ylmethyl)-4-(4-fluorophenyl)piperidine 4a

To a solution of 1-(6-aminoindan-1-ylmethyl)-4-(4-fluorophenyl)piperidine, 2a (6.5 g) and triethylamine (3 ml) in dichloromethane (150 ml) cooled to 0° C. was added dropwise a solution of acetylchloride (1.7 g) in dichloromethane (50 ml). The mixture was stirred for one hour at room temperature. Water (500 ml) was added, the organic phase separated, washed with brine (2×50 ml) and finally worked-up as above. The thus isolated crude title product was purified by column chromatography on silica gel (eluted with a mixture of ethyl acetate/heptane/triethylamine 75:25:4). Recrystallization from diethyl ether yielded 7.7 g of pure title compound 4a. Mp: 159–162° C. $^1$H NMR (CDCl$_3$): δ 1.70–1.90 (m, 5H); 2.00–2.15 (m, 1H); 2.15 (s, 3H); 2.20–2.30 (m, 1H); 2.35–2.50 (m, 2H); 2.60 (dd, 1H); 2.70–2.90 (m, 2H); 2.95–3.15 (m, 2H); 3.45 (qui, 1H); 6.95 (t, 2H); 7.05–7.25 (m, 5H); 7.55 (s, 1H)

In a corresponding manner, the following acylamino, thioacylamino, and sulfonylamino derivatives were prepared:

1-(6-Acetylaminoindan-1-ylmethyl)-4-(4-fluorophenyl) piperazine 4b, mp: 179–187° C. (ethanol). $^1$H NMR (DMSO-d$_6$): δ 1.70–1.85 (m, 1H); 2.00 (s, 3H); 2.10–2.25 (m, 1H); 2.35 (dd, 1H), 2.50–2.60 (m, 5H); 2.65–2.90 (m, 2H); 3.10 (t, 4H); 3.35 (qui, 1H); 6.90–7.10 (m, 5H);7.30 (d, 1H); 7.60 (s, 1H); 9.75 (s, 1H)

1-(5-Acetylamino-2,3-dihydrobenzothiophen-3-ylmethyl)-4-(4-fluorophenyl)piperidine 4c, mp: 140–142° C. (washed with diethyl ether). $^1$H NMR (DMSO-d$_6$): δ 1.55–1.75 (m, 4H); 1.95 (s, 3H); 1.90–2.05 (m, 1H); 2.05–2.20 (dt, 1H); 2.35 (dd, 1H); 2.40–2.55 (m, 2H); 2.95 (d, 1H), 3.15 (d, 1H); 3.20–3.35 (m, 1H); 3.45 (t, 1H); 3.55–3.70 (m, 1H); 7.05–7.15 (m, 3H); 7.25–7.35 (m, 3H); 7.65 (s, 1H); 9.85 (s, 1H)

1-(6-Acetylaminoindan-1-ylmethyl)-4-(4-chlorophenyl) piperazine 4d, mp: 191–194° C. (acetone). $^1$H NMR (CDCl$_3$): δ 1.80–1.95 (m, 1H); 2.10 (s, 3H); 2.20–2.35 (m, 1H); 2.45 (dd, 1H); 2.60–2.70 (m, 5H); 2.80–2.95 (m, 2H); 3.15 (t, 4H); 3.35 (qui, 1H); 6.85 (d, 2H); 7.05–7.25 (m, 5H); 7.55 (s, 1H);

1-(6-Acetylaminoindan-1-ylmethyl)-4-(3-chlorophenyl) piperazine 4e, mp: 176–178° C. (acetone), $^1$H NMR (CDCl$_3$): δ 1.75–1.90 (m, 1H), 2.15 (s, 3H); 2.20–2.35 (m, 1H); 2.45 (dd, 1H); 2.60–2.75 (m, 5H); 2.75–2.95 (m, 2H); 3.20 (t, 4H); 3.35 (qui, 1H); 6.80 (d, 2H); 6.85 (s, 1H); 7.10–7.30 (m, 4H); 7.55 (s, 1H)

1-(6-Acetylaminoindan-1-ylmethyl)-4-(2-chlorophenyl) piperazine, hydrochloride, 4f mp: 195–203° C. (acetone). $^1$H NMR (DMSO-d$_6$): δ 2.00(s, 3H); 2.00–2.15 (m, 1H); 2.30–2.45 (m, 1H); 2.75–2.95 (m, 2H); 3.20–3.80 (m, 11H); 7.05–7.40 (m, 5H); 7.45 (d, 1H); 7.65 (s, 1H); 10.00 (s, 1H); 10.95 (broad s, 1H)

1-(6-Acetylaminoindan-1-ylmethyl)-4-(2-methoxyphenyl)piperazine, oxalate 4g, mp: 210–213° C. (acetone/ethanol 1:1), $^1$H NMR (DMSO-d$_6$): δ 1.85–2.00 (m, 1H); 2.05 (s, 3H); 2.25–2.40 (m, 1H); 2.65–3.05 (m, 3H); 3.25 (broad s, 8H); 3.45–3.60 (m, 1H); 3.80 (s, 3H); 6.85–7.05 (m, 4H); 7.15 (d, 1H); 7.30 (d, 1 H); 7.60 (s, 1H); 9.90 (s, 1H)

1-(6-Acetylaminoindan-1-ylmethyl)-4-(4-fluorophenyl)-1,2,3,6-tetrahydropyridine 4h, mp: 156–161° C. (washed with diethyl ether). $^1$H NMR (CDCl$_3$); δ 1.80–1.95 (m, 1H); 2.15 (s, 3H); 2.20–2.35 (m, 1H); 2.45–2.60 (m, 3H); 2.65–3.00 (m, 5H); 3.20 (broad s, 2H); 3.30–3.45 (m, 1H); 6.05 (broads, 1H); 6.95 (t, 2H); 7.15 (d, 1H); 7.15–7.25 (m, 2H); 7.35 (dd, 2H); 7.50 (s, 1H)

4-(4-Fluorophenyl)-1-(6-methansulfonylaminoindan-1-ylmethyl)piperidine 4i, mp 152–155° C. (diethyl ether), $^1$H NMR (CDCl$_3$): δ 1.70–1.90 (m, 5H); 2.00–2.20 (m, 2H); 2.20–2.35 (m, 1H); 2.40–2.70 (m, 3H); 2.75–2.95 (m, 2H); 3.00 (s, 3H); 3.10 (t, 2H); 3.25–3.45 (m, 1H); 6.70 (broad s, 1H); 6.90–7.05 (m, 3H); 7.15–7.25 (m, 3H); 7.35 (s, 1H)

1-(6-Cyclopropylcarbonylaminoindan-1-ylmethyl)-4-(4-fluorophenyl)piperidine 4j, mp: 134–140° C. (diethyl ether), $^1$H NMR (CDCl$_3$): δ 0.75–0.90 (m, 2H); 1.05–1.15 (m, 2H); 1.45–1.60 (m, 1H); 1.75–1.95 (m, 6H); 2.00–2.15 (m, 2H); 2.20–2.35 (m, 1H); 2.35–2.50 (m, 2H); 2.65 (dd, 1H); 2.70–2.95 (m, 2H); 3.00–3.15 (m, 2H); 3.35 (qui, 1H); 6.95 (t, 2H); 7.05–7.25 (m, 4H); 7.40 (broad s, 1H); 7.65 (broad s, 1H)

1-(6-Cyclopentylcarbonylaminoindan-1-ylmethyl)-4-(4-fluorophenyl)piperidine 4k, mp: 177–178° C. (diethyl ether). $^1$H NMR (CDCl$_3$): δ 1.50–1.70 (m, 2H); 1.70–1.95 (m, 11H); 2.00–2.15 (m, 2H); 2.20–2.35 (m, 1H); 2.35–2.50 (m, 2H); 2.60–2.75 (m, 2H); 2.75–2.95 (m, 2H); 2.95–3.15 (m, 2H); 3.35 (qui, 1H); 6.95 (t, 2H); 7.10–7.25 (m, 5H); 7.65 (s, 1H)

1-(6-Ethyloxycarbonylaminoindan-1-ylmethyl)-4-(4-fluorophenyl)piperidine, fumarate 4l, mp:191–193° C. (ethanol/acetone 2:1).$^1$H NMR (DMSO-d$_6$); δ 1.15 (s, 3H); 1.70–1.90 (m, 5H); 2.10–2.30 (m, 3H); 2.40–2.90 (m, 5H); 3.10–3.20 (m, 2H); 3.25–3.35 (m, 1H); 4.15 (q, 1H); 6.60 (s, 1.5H); 7.00–7.15 (m, 4H); 7.35 (dd, 2H); 7.55 (s, 1H); 9.45 (s, 1H).

4-(4-Chlorophenyl)-1-(6-methansulphonylaminoindan-1-ylmethyl)-1,2,3,6-tetrahydropyperidine, oxalate 4m, mp: 176–178° C. (from ethanol), $^1$H NMR (DMSO-d$_6$): δ 1.90–2.00 (m, 1H); 2.30–2.40 (m, 1H); 2.95 (s, 3H); 2.65–3.10 (m, 5H); 3.20–3.30 (m, 3H); 3.50–3.60 (m, 1H); 3.75 (broad s, 2H); 6.25 (broad s, 1H); 7.05 (dd, 1H); 7.15–7.25 (m, 2H); 7.45 (d, 2H); 7.55 (d, 2H); 9.60 (broad s, 1H).

1-(6-Acetylaminoindan-1-ylmethyl)-4-(4-methylphenyl) piperidine 4n, mp: 173–175° C. (washed with diethyl ether), $^1$H NMR (CDCl$_3$): δ 1.70–1.95 (m, 5H); 2.10 (s, 3H); 2.20–2.30 (m, 1H); 2.30 (s, 3H); 2.35–2.50 (m, 2H); 2.65 (dd, 1H); 2.70–2.90 (m, 2H); 3.00–3.15 (m, 2H); 3.35 (qui, 1H); 7.05–7.25 (m, 6H); 7.50 (s, 1H); 7.55 (s, 1H).

1-(6-Acetylaminoindan-1-ylmethyl)-4-(3,4-dichlorophenyl)piperazine 4o, mp: 160–163° C. (washed with diethyl ether), $^1$H NMR (CDCl$_3$): δ 1.80–1.90 (m, 1H); 2.10 (s, 3H); 2.15–2.30 (m, 1H); 2.45 (dd, 1H); 2.55–2.70 (m, 5H); 2.70–3.00 (m, 2H); 3.20 (t, 4H); 3.35 (qui, 1H); 6.25 (d, 1H); 6.95 (d, 1H); 7.10 (d, 1H); 7.20 (dd, 1H); 7.25 (d, 1H); 7.40 (broads, 1H); 7.60 (s, 1H).

1-(6-Acetylaminoindan-1-ylmethyl)-4-(4-chlorophenyl)-1,2,3,6-tetrahydropyridine, oxalate 4p, mp; 223–226° C. (from acetone), $_1$H NMR (OMSO-ds): δ 1.80–1.95 (m, 1H); 2.05 (s, 3H); 2.20–2.40 (m, 1H); 2.65–3.00 (m, 5H); 3:15–3.30 (m, 3H); 3.50–3.60 (m, 1H); 3.70 (broad s, 2H); 6.25 (broad s, 1H); 7.15 (d, 1H); 7.30 (d, 1H); 7.40 (d, 2H); 7.50 (d, 2H); 7.65 (s, 1H).

1-(6-Acetylaminoindan-1-ylmethyl)-4-(3,4-methylenedioxyphenyl)piperazine, 4q, mp: 188–189° C. (washed with diethyl ether). $^1$H NMR (CDCl$_3$): δ 1.70–1.95 (m, 1H); 2.15 (s, 3H); 2.15–2.30 (m, 1H); 2.45 (dd, 1H); 2.60–2.70 (m, 5H); 2.70–2.90 (m, 2H); 3.10 (t, 4H); 3.40 quin, 1H); 5.85 (s, 2H); 6.45 (dd, 1H); 6.55 (d, 1H); 6.70 (d, 1H); 7.15 (d, 1H); 7.20–7.35 (m, 2H); 7.55 (s, 1H).

1-(6-Acetylaminoindan-1-ylmethyl)-4-hydroxy-4-(3-trifluoromethyl-4-chlorophenyl)piperidine, hemioxalate, 4r, mp: 163–165° C. (acetone). $^1$H NMR (DMSO-d$_6$): δ 1.65–1.95 (m, 3H); 2.05 (s, 3H); 2.15–2.30 (m, 3H); 2.65–3.30 (m, 8H); 3.40–3.50 (m, 1H); 7.15 (d, 1H); 7.25 (d, 1H); 7.70–7.65 (m, 3H); 8.00 (s, 1H).

EXAMPLE 5

(Method a)

4-(4-Fluorophenyl)-1-(6-methylaminocarbonylaminoindan-1-ylmethyl)piperidine, 5a 1-(6-Aminoindan-1-ylmethyl)-4-(4-fluorophenyl)piperidine, 2a (3 g) was dissolved in dichloromethane (140 ml) and methylisocyanate (0.53 g) was added. The solution was refluxed for 4 hours. Dichloromethane was evaporated and the remaining crude title compound was purified by column chromatography on silica gel (eluted with 4% triethylamine in ethyl acetate). The pure title compound 5a crystallized from diethyl ether. Yield : 0.8 g, mp: 170–173° C. 1H NMR (CDCl$_3$): δ 1.70–1.90 (m, 5H); 2.00–2.15 (m, 2H); 2.20–2.35 (m, 1H); 2.35–2.55 (m, 2H); 2.60 (dd, 1H); 2.80 (d, 3H); 2.75–2.95 (m, 2H); 3.05 (broad d; 2H); 3.30 (qui, 1H); 4.95 (q, 1H); 6.55 (s, 1H); 6.90–7.00 (m, 3H); 7.10–7.25 (m, 3H); 7.35 (s, 1H)

In a similar manner the following urea or thiourea derivatives were prepared

1-[6-(4-Fluorophenyl)aminocarbonylaminoindan-1-ylmethyl]-4-(4-fluorophenyl)-piperidine, 5b, mp: 235–238° C. (CH$_2$Cl$_2$). $^1$H NMR (DMSO-d$_6$); 1.55–1.80 (m, 5H); 2.00–2.30 (m, 3H); 2.35 (dd, 1H); 2.45–2.60 (m, 2H); 2.60–2.85 (m, 2H); 3.05 (broad d, 2H); 3.30 (qui, 1H); 7.05–7.15 (m, 6H); 7.25–7.35 (dd, 2H); 7.40–7.50 (dd, 2H); 7.55 (s, 1H); 8.50 (s, 1H); 8.65 (s, 1H)

4-(4-Fluorophenyl)-1-(6-methylaminothiocarbonylaminoindan-1-ylmethyl)piperidine, fumarate, 5c, mp: 181–183° C. (ethanol/acetone 1:1). $^1$H NMR (DMSO-d$_6$): δ 1.70–1.90 (m, 5H); 2.15–2.95 (m, 8H); 2.90 d, 3H); 3.20–3.30 (m, 2H); 3.40 (qui, 1H); 6.20 (s, 2H); 7.05–7.20 (m, 4H); 7.30 (dd, 2H); 7.40 (s, 1H); 7.80 (broad s, 1H); 9.60 (broad s, 1H).

1-(6-Methylaminocarbonylaminoindan-1-yl methyl)-4-(3,4-methylendioxyphenyl)piperazine, hemioxalate, 5d, mp: 132–133° C. (acetone). $^1$H NMR (DMSO-d 6): δ 1.70–1.85 (m, 1H); 2.15–2.30 (m, 1H); 2.60 (d, 3H); 2.70–3.00 (m, 7H); 3.20 (m, 4H); 3.35–3.45 (m, 1H); 5.90 (s, 2H); 6.00–6.10 (m, 1H); 6.40 (dd, 1H); 6.70 (d, 1H); 6.80 (d, 1H); 7.05 (d, 1H); 7.10 (d, 1H); 7.45 (s, 1H); 8.40 (s, 1H).

EXAMPLE 6

(Method a)

1-(6-Dimethylaminocarbonylaminoindan-1-ylmethyl)-4-(4-fluorophenyl)piperidine, 6a 1-(6-Aminoindan-1-ylmethyl)-4-(4-fluorophenyl)piperidine, 2a (3 g) was dissolved in THF (50 ml) and triethylamine (2 g) was added. At 5° C. dimethylcarbamoylchloride (1 g) in THF (15 ml) was added dropwise. After completed addition the mixture was refluxed for 1.5 hours. THF was evaporated. Water was added and extraction with dichloromethane (2×50 ml) and work-up as above of the combined organic phases yielded crude title product, which was purified by column chromatography on silica gel (eluted with 4% triethylamine in a 1:1 mixture of ethyl acetate and heptane). The pure title compound 6a crystallized from diethyl ether. Yield : 1,4 g, mp: 141–144° C. $^1$H NMR (CDCl$_3$): δ 1.65–2.55 (m, 10H); 2.70 (dd, 1H); 2.70–2.95 (m, 2H); 2.95–3.05 (m, 1H); 3.05 (s, 6H); 3.15 (broad d, 1H); 3.35 (qui, 1H); 6.25 (s, 1H); 6.95–7.25 (m, 6H); 7.45 (s, 1H)

In a similar manner the following urea and thiourea derivatives were prepared:

1-(6-Dimethylaminothiocarbonylaminoindan-1-ylmethyl)-4-(4-fluorophenyl)piperidine 6b, mp: 175–180° C. (washed with diethyl ether). $^1$H NMR (CDCl$_3$): δ 1.65–1.95 (m, 5H); 2.00–2.15 (m, 2H); 2.20–2.35 (m, 1H); 2.35–2.55 (m, 2H); 2.60 (dd, 1H); 2.70–2.90 (m, 2H); 3.05–3.15 (m, 2H); 3.85 (s, 6H); 3.40 (qui, 1H); 6.95–7.10 (m, 4H); 7.15–7.30 (m, 4H)

4-(4-fluorophenyl)-1-[6-(1-pyrrolidinyl)carbonylaminoindan-1-ylmethyl]piperidine 6c, mp: 190–193° C. (washed with diethyl ether). $^1$H NMR (CDCl$_3$): δ 1.65–2.55 (m, 14H); 2.65 (dd, 1H); 2.75–2.90 (m, 2H); 3.00 (broad d, 1H); 3.15 (broad d, 1H); 3.35 (qui, 1H); 3.45 (t, 4H); 6.15 (s, 1H); 6.95 (t, 2H); 7.00–7.10 (m, 2H); 7.20 (dd, 2H); 7.50 (s, 1H)

EXAMPLE 7

(Method a)

1-(6-Aminocarbonylaminoindan-1-ylmethyl)-4-(4-fluorophenyl)piperidine, hemifumarate, 7a A solution of potassium isocyanate (1.5 g) dissolved in dichloromethane (20 ml) was cooled to 5° C. and a solution of trifluoroacetic acid (1.9 g) In dichloromethane (20 ml) was added dropwise. To the resulting mixture was added dropwise a solution of 1-(6-aminoindan-1-ylmethyl)-4-(4-fluorophenyl)piperidine, 2a (3 g) in dichloromethane (10 ml). The temperature was allowed to raise to room temperature. After stirring for another 3 hours the mixture was poured on ice (500 g) and diluted aqueous NH$_4$OH was added until pH>9. The organic phase was separated and worked-up as above. The crude title product was purified by column chromatography on silica gel (eluted with 4% triethylamine in ethanol/ethyl acetate 1:3). The purled product (2 g) was dissolved in acetone (20 ml) and added to a solution of fumaric acid (0.6 g) in ethanol (20 ml). The precipitated hemifumarate salt was filtered off and dried. Yield: 1.6 g, mp: 172–174° C. $^1$H NMR (DMSO-d$_6$): δ 1.65–1.90 (m, 5H); 2.10–2.35 (m, 3H); 2.45–2.90 (m, 5H); 3.10–3.25 (m, 2H); 3.45 (qui, 1H); 6.85 (s, 2H); 6.60 (s, 1H); 7.00–7.15 (m, 4H); 7.30 (dd, 2H); 7.45 (s, 1H); 8.45 (s, 1H).

EXAMPLE 8

5-Chloro-3-(1,2,3,6-tetrahydropyridine-4-yl)-1H-indole, 8a

A mixture of 5-chloro-1H-indole (25 g), piperidin-4-one, hydrate, hydrochloride (71 g), and potassium hydroxide (38 g) in ethanol (450 ml) was refluxed for 6 hours. After cooling inorganic salts were filtered off and ethanol evaporated in vacuo. To the remaining oil was added brine (500 ml) and ethyl acetate (2×200 ml). The organic phase was separated and worked-up as above. Yield of crude title product: 45 g (semicrystalline).

In a corresponding manner the following 3-(1,2,3,6-tetrahydropyridine-4-yl)-1H-indoles were prepared:

6-Chloro-3-(1,2,3,6-tetrahydropyridin-4-yl)-1H-Indole, 8b
5-Fluoro-3-(1,2,3,6-tetrahydropyridin-4-yl)-1H-indole, 8c

EXAMPLE 9

5-Chloro-3-(4-piperidinyl)-1H-indole, 9a

Crude 5-chloro-3-(1,2,3,6-tetrahydropyridin-4-yl)-1 H-indole 8a (26 g) was dissolved in glacial acetic acid (330 ml) and $PtO_2$ (0.7 g) was added. The mixture was hydrogenated in a Parr apparatus at 3 atm. for 5 hours. The catalyst was filtered off and excess acetic acid evaporated in vacuo. Water was added and pH was adjusted to >9 by addition of diluted aqueous $NH_4OH$ Extraction with ethyl acetate (2×200 ml) and work-up of the combined organic phases yielded 19 g of crude title compound as a viscous oil.

In a corresponding manner the following 3-(4-piperidinyl)-1H-indoles were prepared:
6-Chloro-3-(4-piperidinyl)-1H-indole, 9b
5-Fluoro-3-(4-piperidinyl)-1H-Indole, 9c

EXAMPLE 10

3-[1-(5-Amino-2,3-dihydrobenzothiophen-3-ylmethyl)piperidin-4-yl]-5-chloro-1H-indole, 10a 5-Nitro-3-benzothiophencarboxylic acid 1b (20 g) was converted into the corresponding carboxylic acid chloride as in Example 2. The acid chloride was dissolved in THF (200 ml) and added dropwise to a solution of 5-chloro-3-(4-piperidinyl)-1H-indole, 9a (19 g) and triethylamine (10 ml) in THF (200 ml) at 0–5° C. The mixture was stirred overnight at room temperature. THF was evaporated. Water was added to the remaining oil. Extraction with dichloromethane (2×100 ml) and work-up of the organic extracts afforded the crude 5-nitro-3-benzothiophencarboxylic acid amide, which was subsequently purified by column chromatography on silica gel (eluted with ethyl acetate/heptane 1:1). Yield 6.6 g, mp: 243–250° C. All of the amide was dissolved in 90% ethanol at reflux. Fe-powder (5 g) and concentrated aqueous HCl were added successively in small portions during 10 minutes. The mixture was refluxed for another 2.5 hours. Inorganic sags were filtered off and ethanol evaporated in vacuo. Water was added to the remaining oil and pH was adjusted to >9 by addition of diluted aqueous $NH_4OH$ Extraction with dichloromethane (2×100 ml) and subsequent work-up of the organic phase yielded 4 g of the 5-amino-3-benzothiophencarboxylic acid amide as an oil. All of this oil was dissolved in methanol (100 ml). 0.5 g of Mg turnings were added. By heating to 35° C. an exothermic reaction started. Mg turnings were added in small portions (3×0.5 g) while keeping the temperature below 45° C. The mixture was finally poured into an aqueous $NH_4Cl$ solution and concentrated aqueous HCl (1 ml) was added. Extraction with dichloromethane (2×50 ml) and work-up of the organic extracts as above afforded 2 g of the 5-amino-2,3-dihydrobenzothiophen-3-carboxylic acid amide as an oil. To a suspension of $LiAlH_4$ (0.6 g) in dry THF (50 ml). The mixture was gently refluxed for 2 hours. After cooling to 10° C. water (2.4 ml) and a 15% aqueous NaOH solution were cautiously added to destroy excess $LiAlH_4$. Inorganic salts were filtered off and washed extensively with THF. The combined THF solutions were evaporated leaving 1.9 g of 3-[1-(5-amino-2,3-dihydrobenzothiophen-3-ylmethyl)piperidin-4-yl]-5-chloro-1H-indole as an oil.

In a similar manner the following aniline derivatives were prepared:

3-[1-(5-Amino-2,3-dihydrobenzothiophen-3-ylmethyl)-1,2,3,6-tetrahydropyridin-4-yl]-5-chloro-1H-indole, 10b as an oil
3-[1-(5-Amino-2,3-dihydrobenzothiophen-3-ylmethyl)-1,2,3,6-tetrahydropyridin-4-yl]-5-fluoro-1H-indole, 10c as an oil.

The corresponding 1-(6-Aminoindan-1-ylmethyl)-substituted 4-(3-indolyl)piperidines and 4-(3-indolyl)-1,2,3,6-tetrahydropyridines were prepared from the corresponding 1-indancarboxamides, which were successively nitrated in the 6 position, reduction of the nitro substituent and reduction of the carboxamide carbonyl group. A reaction sequence as outlined in Example 3. The following indan derivatives were prepared accordingly:
3-[1-(6-Aminoindan-1-ylmethyl)piperidin-4-yl]-5-fluoro-1H-indole, 10d as an oil.
3-[1-(6-Aminoindan-1-ylmethyl)piperidin-4-yl]-6-chloro-1H-indole, 10e as an oil.
3-[1-(6-Aminoindan-1-ylmethyl)-1,2,3,6-tetrahydropyridin-4-yl]-5-chloro-1H-indole, 10f as an oil.
3-[1-(6-Aminoindan-1-ylmethyl)-1,2,3,6-tetrahydropyridin-4-yl]-6-chloro-1H-indole, 10g as an oil.
1-[1-(6-aminoindan-1-ylmethyl)piperidin-4-yl]-5-chloro-1H-indole, 10H as an oil.

EXAMPLE 11

3-[1-(5-Acetylamino-2,3-dihydrobenzothiophen-3-ylmethyl)piperidin-4-yl]-5-chloro-1H-indole, oxalate, 11a To a solution of 3-[1-(5-amino-2,3-dihydrobenzothiophen-3-ylmethyl)piperidin-4-yl]-5-chloro-1H-indole 10a (1.9 g) and triethylamine (2 ml) in dichloromethane (50 ml) kept at 0° C. was added dropwise a solution of acetylchloride (0.4 g) in dichloromethane (10 ml). The mixture was stirred at room temperature for 2 hours. Water was added and the organic phase was worked-up as above. The crude title compound was purified by column chromatography on silica gel (eluted with 4% triethylamine in ethyl acetate). Yield: 0.8 g. The oxalate salt of the title compound crystallized from a 1:1 mixture of acetone and ethanol. Mp: 168–174° C. $^1H$ NMR (DMSO-$d_6$): δ 2.00 (s, 3H); 1.95–2.15 (m, 4H); 2.85–3.25 (m, 5H); 3.40–3.50 (m, 2H); 3.55–3.70 (m, 2H);3.90–4.00 (m, 1H); 7.00–7.40 (m, 6H); 7.70 (s, 1H); 7.70 (broad s, 2H); 9.95 (broad s, 1H);11.10 (broad s, 1H), In a similar manner the following indolyl derivatives were prepared:

3-[1-(5-Acetylamino-2,3-dihydrobenzothiophen-3-ylmethyl)-1,2,3,6-tetrahydropyridin-4-yl]-5-chloro-1H-indole, oxalate 11b, mp: 214–216° C. (ethanol), $^1H$ NMR (DMSO-$d_6$): δ 2.00 (s, 3H); 2.75 (broad s, 2H); 2.95–3.40 (m, 5H); 3.50–3.80 (m, 3H); 3.95 (broad s, 1H); 6.15 (broad s, 1H); 7.15 (t, 2H); 7.25 (d, 1H);7.45 (d, 1H); 7.60 (s, 1H); 7.65 (s, 1H); 7.85 (s, 1H); 9.95 (s, 1H); 11.50 (s, 1H)

3-[1-(6-Acetylaminoindan-1-ylmethyl)piperidin-4-yl]-5-fluoro-1H-indole, oxalate 11c, mp: 145–149° C. (acetone). $^1H$ NMR (DMSO-$d_6$): δ 1.80–2.15 (m, 6H); 2.00 (s, 3H); 2.30–2.45 (m, 1H); 2.70–2.90 (m, 2H); 2.95–3.20 (m, 3H); 3.35 (d, 1H); 3.50–3.80 (m, 3H); 6.95 (dt, 1H); 7.15 (d, 1H); 7.25 (s, 1H); 7.30 (d, 1H); 7.40 (dd, 1H); 7.45 (dd, 1H); 7.70 (s, 1H); 9.95 (s, 1H);11.05 (s, 1H)

3-[1-(5-Acetylamino-2,3-dihydrobenzothiophen-3-ylmethyl)-1,2,3,6-tetrahydropyridin-4-yl]-5-fluoro-1H-indole, oxalate 11d, mp: 155–165° C. (acetone). $^1H$ NMR (DMSO-$d_6$): δ 2.00 (s, 3H); 2.75 (broad s, 2H); 2.95–3.45

(m, 5H); 3.50–3.80 (m, 3H); 3.95 (broad s, 1H); 6.15 (broad s, 1H); 6.95 (t, 1H); 7.20 (d, 1H); 7.30 (d, 1H);7.45 (m, 1H); 7.55–7.70 (m, 3H); 9.95 (s, 1H); 11.45 (s, 1H)

3-[1-(6-Acetylaminoindan-1-ylmethyl)-1,2,3,6-tetrahydropyridin-4-yl]-6-chloro-1H-indole, oxalate hemihydrate 11e, mp: 151–164° C. (acetone). $^1$H NMR (DMSO-d$_6$): δ 1.95–2.10 (m, 1H); 2.00 (s, 3H); 2.30–2.45 (m, 1H); 2.70–2.90 (m, 4H); 3.15 (t, 1H); 3.35–3.50 (m, 3H); 3.55–3.70 (m, 1H); 3.95 (broad s, 2H); 6.15 (s, 1H); 7.05 (dd 1H); 7.15 (d, 1H); 7.25 (d, 1H); 7.45 (d, 1H); 7.55 (d, 1H); 7.60 (s, 1H); 7.85 (d, 1H); 9.95 (s, 1H); 11.55 (s, 1H)

3-[1-(6-Acetylaminoindan-1-ylmethyl)piperidin-4-yl]-6-chloro-1H-indole,oxalate 11f, mp: 122–130° C. (acetone). $^1$H NMR (DMSO-d$_6$): δ 1.90–2.15(m, 6H); 2.00 (s, 3H); 2.25–2.40(m, 1H); 2.70–3.10 (m, 6H); 3.35 (d, 1H); 3.45–3.65 (m, 2H); 7.00 (dd, 1H); 7.15–7.25 (m, 2H); 7.30 (d, 1H); 7.40 (s, 1H); 7.60–7.70 (m, 2H); 9.90 (s, 1H); 11.05 (s, 1H)

3-[1-(6-Acetylaminoindan-1-ylmethyl)-1,2,3,6-tetrahydropyridin-4-yl]-5-chloro-1H-indole, oxalate 11g, mp: 220–223° C. (acetone/ethanol 5:1). $^1$H NMR (DMSO-d$_6$); δ 1.95–2.10 (m, 1H); 2.00 (s, 3H); 2.30–2.45 (m, 1H); 2.70–2.95 (m, 4H); 3.10 (t, 1H); 3.30–3.45 (m, 3H); 3.55–3.70 (m, 1H); 3.85 (broad s, 2H); 6.15 (s, 1H); 7.10–7.20 (m, 2H); 7.30 (d, 1H); 7.45 (d, 1H); 7.60–7.70 (m, 2H); 7.85 (s, 1H); 9.90 (s, 1H); 11.50 (s, 1H)

1-[1-(6-Acetylaminoindan-1-ylmethyl)piperidin-4-yl]-5-chloro-1H-indole, 11h, mp: 189–191° C. (ethyl acetate), $^1$H NMR (CDCl$_3$): δ 1.80–2.00 (m, 1H); 2.05–2.40 (m, 7H); 2.20 (s, 3H); 2.50 (dd, 1H); 2.65 (dd, 1H); 2.80–2.95 (m, 2H); 3.15 (broad t, 2H); 3.35 (quin, 1H); 4.20–4.30 (m, 1H); 6.45 (d, 1H); 7.20–7.35 (m, 4H); 7.30–7.40 (m, 2H); 7.60 (d, 1H); 7.70 (broad s, 1H).

EXAMPLE 12

(Method e)

4-(4-Fluorophenyl)-1-[6-(1-pyrrolidin-2-onyl)indan-1-ylmethyl]piperidine, fumarate, 12a To a solution of 1-(6-aminoindan-1-ylmethyl)-4-(4-fluorophenyl)piperidine, 2a (3 g) and triethylamine (2 ml) in dichloromethane (50 ml) at 0° C. was added dropwise a solution of 4-chlorobutyric acid chloride (1.4 g) in dichloromethane (15 ml). The mixture was finally stirred for 5 hours at room temperature. Ice cold diluted aqueous NaOH solution was added and the organic phase was subsequently worked-up as above. The crude 1-[6-(4-chlorobutanoylamino)indan-1-ylmethyl]-4-(4-fluorophenyl)-piperidine was purified by column chromatography on silica gel (eluted with 4% triethylamine in a 1:3 mixture of ethyl acetate and heptane). Yield of crystalline product: 2.4 g with mp: 129–135 (washed with diethyl ether). A solution of the thus isolated 4-chlorobutanoyl derivative (1 g) and potassium tert-butoxide (0.4 g) in dry THF (40 ml) was refluxed for 2 hours. THF was evaporated in vacuo. Diluted aqueous NH$_4$OH and dichloromethane were added and the organic phase was subsequently worked-up as above. The remaining oil (1 g) was dissolved in acetone (10 ml) and added to a hot solution of fumaric acid (0.3 g) in ethanol (15 ml). After cooling in a refrigerator overnight the precipitated fumarate salt was filtered off and dried. Yield: 0.7 g, mp: 177–179° C. $^1$H NMR (DMSO-d$_6$): δ 1.70–1.90 (m, 5H); 2.10 (qui, 2H); 2.20–2.40 (m, 3H); 2.45–2.65 (m, 4H); 2.70–2.95 (m, 3H); 3.20 (broad t, 2H); 3.40 (qui, 1H); 3.70–3.90 (m, 2H); 6.60 (s, 2H); 7.15 (t, 2H); 7.20 (d, 1H); 7.30 (dd, 2H); 7.40 (dd, 1H); 7.65 (s, 1H).

EXAMPLE 13

(+)-6-Nitro-1-indancarboxylic acid, 13a

A solution of 6-nitro-1-indancarboxylic acid (1a) (96 g) and brucine dehydrate (200 g) was heated in acetone (1.25 L) until a clear solution was obtained. The solution was left in a refrigerator overnight. The precipitated brucine salt was filtered off. Yield: 159.1 g. Recrystallization from 2-propanol afforded 103 g of pure (+)-6-nitro-1-indancarboxylic acid brucine salt. The salt was dissolved in water and diluted hydrochloric acid was added. Extraction with diethyl ether and work-up as above afforded 29.8 g of 13a. Mp: 92–94° C. [α]=$_D$=+83.3°(c=1, methanol).

EXAMPLE 14

(+)-1-(6-Acetylaminoindan-1-ylmethyl)-4-(4-fluorophenyl)piperidine 14a

The (+)-enantiomer of compound 4a was prepared from (+)-6-Nitro-1-indancarboxylic acid, 13a according to the methods in Examples 2 and 4. Mp: 145–146° C., 1H NMR (CDCl$_3$): δ 1.70–1.90 (m, 5H); 2.00–2.15 (m, 1H); 2.15 (s, 3H); 2.20–2.30 (m, 1H); 2.35–2.50 (m, 2H); 2.60 (dd, 1H); 2.70–2.90 (m, 2H); 2.95–3.15 (m, 2H); 3.45 (qui, 1H); 6.95 (t, 2H); 7.05–7.25 (m, 5H); 7.55 (s, 1H). [α]$_D$=+24.3°(c=1, methanol).

EXAMPLE 15

3-[1-(6-Acetylaminoindan-1-ylmethyl)-1,2,3,6-tetrahydropyridin-4-yl]-6-chloro-1-methyl-1H-indole 15a 3-[1-(6-nitroindan-1-ylkarbonyl)-1,2,3,6-tetrahydropyridin-4-yl]-6-chloro-1H-indole (23 g), prepared according to the procedure in Example 10, was dissolved in dry DMF (300 ml) and potassium tert-butoxide (7.3 g) was added at 10° C. Methyliodide (23.2 g) was added dropwise during 30 min. The mixture was left at room temperature overnight. Water and diethyl ether were added and the organic phase was worked-up as above. The crude N-methylated indole was purified by column chromatography on silica gel (eluted with a 1:1 mixture of ethyl acetate and heptane). Yield 2.75 g. Reduction of the nitro group with Fe in 90% acidic ethanol, followed by reduction of the amide carbonyl group and finally acetylation of the anilino group according to the methods in Examples 10 and 11 affords the title compound 15a. Mp: 189–193° C. (washed with diethyl ether). $^1$H NMR (CDCl$_3$): δ 1.80 (broad s, 1H); 1.80–1.95 (m, 1H); 2.10 (s, 3H); 2.25–2.40 (m, 1H); 2.50–2.60 (m, 3H); 2.70–2.95 (m, 5H); 3.25 (broad s, 2H); 3.40 (qui, 1H); 3.70 (s, 3H); 6.15 (broad s, 1H); 7.00 (s, 1H); 7.10 (dd, 1H); 7.15 (d, 1H); 7.20–7.30 (m, 3H); 7.50 (s, 1H); 7.80 (d, 1H).

Catalytic hydrogenation of compound 15a according to the method in Example 9 afforded:

3-[1-(6-Acetylaminoindan-1-ylmethyl)piperidin-4-yl]-6-chloro-1-m ethyl-1H-indole, oxalate 15b, mp: 202–205° C. (acetone). $^1$H NMR (DMSO-d$_6$): δ 1.90–2.15 (m, 5H); 2.00 (s, 3H); 2.30–2.40 (m, 1H); 2.70–3.15 (m, 6H); 3.35 (d, 1H); 3.50–3.70 (m, 2H); 3.75 (s, 3H); 7.00 (dd, 1H); 7.10–7.30 (m, 3H); 7.55 (d, 1H); 7.65 (s, 1H); 7.65 (d, 1H); 9.90 (s, 1H).

EXAMPLE 16

(Method f)

4-(4-Fluorophenyl)-1-(6-methylaminoindan-1-ylmethyl)piperidine, 1.5 oxalate 16a

To a solution of 4-(4-fluorophenyl)-1-(6-methylaminoindan-1-ylmethyl)piperidine, 2a (4 g) and triethylamine (3 mL) in dichloromethane was added dropwise at 0–5° C. a solution of ethyl chloroformate (1.5 g) in dichloromethane (15 mL). The mixture was stirred at room temperature for 2 hours and poured onto saturated brine (500 mL). The organic phase was separated and worked-up as previously. Yield of the ethyl carbamate as an oil 4.3 g. To a suspension of LiAlH$_4$ (1.2 g) in dry diethyl ether (20 mL) at 5° C. was added dropwise a solution of all of the ethyl carbamate in dry THF (25 mL). The mixture was stirred for an additional hour at 5° C. and finally at room temperature for 5 hours. Excess of LiAlH$_4$ was destroyed by cautiously adding water and diluted aqueous NaOH solution (6 ml). Precipitated inorganic sales were filtered off and the solvents evaporated in vacuo. The crude title compound was purified by column chromatography on silica gel (eluted with a 1:1 mixture of heptane and ethyl acetate). Yield as an oil 1.5 g. The 1.5 oxalate salt 16a crystallized from a 1:1 mixture of acetone and ethanol. Mp: 84–86° C. $^1$H NMR (DMSO-d$_6$): δ 1.75–2.10 (m, 5H); 2.20–2.40 (m, 1H); 2.60 (s, 3H); 2.60–2.90 (m, 3H); 3.00–3.15 (m, 3H); 3.40–3.80 (m, 4H); 6.40(dd, 1H); 6.50 (d, 1H); 6.95 (d, 1H); 7.15 (t, 2H); 7.35 (dd, 2H)

EXAMPLE 17

5-Chloro-1-(4-piperidinyl)-1H-indole, 17a

To a solution of 5-chloro-1H-indole (20 g) in N-methyl-2-pyrrolidone (450 mL) were added potassium carbonate (82 g), CuBr (7.5 g), and Cu bronze (3 g). The mixture was heated to 140° C. and 4-bromopyridine, hydrochloride (22 g). The mixture was heated for 1 hour at 150° C. and further 4-bromopyridine, hydrochloride (15 g) was added. This procedure was repeated twice and the mixture was finally heated overnight at 150° C. After cooling precipitated inorganic salts were filtered off. Water (2 L), ethyl acetate (500 mL), and diluted aqueous ammonia (200 mL) were added. Undissolved material was filtered off and discarded. The organic phase was worked-up as above affording 34 g of 5-chloro-1-(4-pyridyl)-1H-indole with mp: 153–155° C. All of this product, without further purification, was dissolved in dimethoxyethane (350 mL) at 60–70° C. Methyliodide (14 mL) was added and the mixture was heated at reflux for 7 hours. After cooling the precipitated quatemized pyrdinium salt was filtered off and washed with dimethoxyethane. Yield 32 g. Mp: 257–260° C. All of the pyridinium salt was suspended in ethanol (450 mL) and water (50 mL). NaBH$_4$ (16 g) was added in small portions during 1.5 hours with stirring. After stirring for another 1.5 hours most of the ethanol was evaporated at room temperature in vacuo. Ethyl acetate (300 mL) and water (500 mL) were added and the organic was worked up as previously. Yield of 5-chloro-1-(1-methyl-1,2,3,6-tetrahydro-4-pyridinyl)-1H-indole, 17 g as an oil. To a solution of the tetrahydropyridinyl (15 g) derivative in glacial acetic acid (150 mL) was added PtO$_2$ and the mixture was hydrogenated in a Parr apparatus at 3 ato for 7 hours. The catalyst was filtered off, most of the acetic acid evaporated in vacuo and finally the crude 5-chloro-1-(1-methyl-4-piperidinyl)-1H-indole was extracted with ethyl acetate from an alkaline aqueous solution. Yield 13 g as an oil. Any remaining water in this crude product (10 g) was removed by evaporation with toluene. Finally the oil was dissolved in 1,1,1-trichloroethane (200 ml.). At reflux temperature 2,2,2-trichloroethyl chloroformate (6.5 mL) dissolved in 1,1,1-trichloroethane (20 ml) was added dropwise. The mixture was refluxed for another 2 hours, sodium carbonate (2 g) was added and reflux continued for 0.5 hours. After cooling the mixture was filtered through silicagel (eluted with dichloromethane). Yield 10 g of crude carbamate derivative. To a solution of the carbamate (6 g) in 90% aqueous acetic acid (110 mL) was added finely powdered Zn (12 g) in small portions at 45° C. during 1 hour. The mixture was heated for another hour at 50° C., Zn-salts were filtered off and most of the acetic acid evaporated in vacuo. The remaining oil was dissolved in water (200 mL) and ethyl acetate (200 mL). The pH of the aqueous phase was adjusted >9 by adding diluted aqueous ammonia. The organic phase was finally worked-up as previously yielding 3.5 g of crude title product 17a as an oil which was used without further purification to prepare compound 10h.

EXAMPLE 18

1-(6-Acetylaminoindan-1-ylmethyl)-4-acetyloxy-4-(3-trifluoromethyl-4-chlorophenyl)piperidine, 18a To a solution of 1-(6-aminoindan-1-ylmethyl)-4-hydroxy-4-(3-t(fluoromethyl-4-chlorophenyl)piperidine, 2j, (6.7 g) and triethylamine (4 mL) in dichloromethane (100 mL) was added dropwise at 0–5° C. a solution of chloroacetylchloride (2.6 mL) in dichloromethane (50 mL). The mixture was stirred overnight at room temperature. Water was added and pH was adjusted to >9. The organic phase was separated and worked up as previously. The crude product was purified by column chromatography on silicagel (eluted with 4% triethylamine in ethyl acetate). Yield of pure 18a 6.2 g as an oil.

EXAMPLE 19

5-Chloro-1-[1-(6-methylaminocarbonylaminoindan-1-ylmethyl)piperidin-4-yl]-1H-indole, 19a To a solution of 1-[1-(6-aminoindan-1-ylmethyl)piperidin-4-yl]-5-chloro-1H-indole, 10h (0.9 g) in dichloromethane (10 mL) was added methylisocyanate (0.2 mL). The mixture was stirred at room temperature for 16 hours. Dichloromethane was evaporated. Upon addition of ethyl acetate the title compound 19a crystallized. The crystalline product was filtered off and dried overnight at 80° C. in vacua. Yield 0.6 g. mp: 193–195° C. $^1$H NMR (DMSO-d$_6$): δ 1.70–1.85 (m, 1H); 1.90–2.35 (m, 7H); 2.35–2.85 (m, 4H); 2.65 (d, 3H); 3.05–3.15 (m, 2H); 3.25 (quin, 1H); 4.35–4.45 (m, 1H); 5.95 (dt, 1H); 6.45 (d, 1H); 7.00–7.20 (m, 3H); 7.50–7.65 (m, 4H); 8.35 (s, 1H).

PHARMACOLOGICAL TESTING

The compounds of the invention were tested in well recognized and reliable methods. The well-known 5-HT$_{2A}$ antagonist MDL 100,907 and the well-known 5-HT$_{1A}$ antagonist buspirone were Included in the tests as reference compounds. The tests were as follows, and the results are given in the following Table 1.

Inhibition of $^3$H-8-OH-DPAT Binding to Serotonin 5-HT$_{1A}$ Receptors In Rat Brain in vitro.

By this method the inhibition by drugs of the binding of the 5-HT$_{1A}$ agonist $^3$H-8-OH-DPAT (1 nM) to 5-HT$_{1A}$ receptors in membranes from rat brain minus cerebellum is determined in vitro . Accordingly, this is a test for affinity for the 5-HT$_{1A}$ receptor. The test is performed as described by Hyttel et al., *Drug. Dev. Res.*, 1988, 15, 389–404.

Inhibition of $^3$H-Ketanserin Binding to 5-HT$_2$ Receptors in Rat Cortex in vitro.

By this method the inhibition by drugs of the binding of $^3$H-Ketanserin (0.5 nM) to 5-HT$_{2A}$ receptors in membranes from rat is determined in vitro. The method is described in Hyttel, *Pharmacology & Toxicology*, 61, 126–129, 1987.

TABLE 1

Binding Data (IC$_{50}$ values in nM or % inhibition of binding at 100 nM)

| Compound No | $^3$H 8-OH DPAT (5-HT$_{1A}$) | $^3$H Ketanserin (5-HT$_{2A}$) |
|---|---|---|
| 2a | 480. | 2.5 |
| 2h | 19%/100. | 4.1 |
| 4a | 11. | 4.0 |
| 4b | 21. | 2.9 |
| 4c | 28. | 2.3 |
| 4d | 12. | 5.0 |
| 4e | 38. | 5.0 |
| 4f | 84. | 65. |
| 4g | 31. | 280. |
| 4h | 11. | 2.8 |
| 4i | 500. | 2.1 |
| 4j | 45. | 15. |
| 4k | 240 | 30. |
| 4l | 26%/100 | 55. |
| 4m | 120. | 2.7 |
| 4n | 27. | 3.9 |
| 4o | 11. | 51. |
| 4p | nt | nt |
| 5a | 35 | 5.1 |
| 5b | >100,000 | 37. |
| 5c | >1000. | 3.9 |
| 6a | 1200 | 9.1 |
| 6b | 1200 | 6.7 |
| 6c | 8200 | 9.9 |
| 7a | 13. | 2.6 |
| 11a | 28. | 42. |
| 11b | 21. | 44. |
| 11c | 16. | 15. |
| 11d | 29. | 15. |
| 11e | 27. | 130. |
| 11f | 8.0 | 21. |
| 11g | 26. | 180. |
| 12a | 340 | 3.5 |
| 14a | 120. | 16. |
| 15a | 91. | 25%/100 |
| 15b | 25%/100 | 300. |
| 16a | 170. | 1.6 |
| buspirone | 41. | 1300. |
| MDL 100,907 | nt$^a$ | 0.51 |

$^a$nt: not tested.

In addition to the above tests, the compounds of the invention were tested with respect to affinity for the dopamine D$_2$ receptor by determining their ability to inhibit the binding of $^3$H-spiroperidol to D$_2$ receptors by the method of Hyttel et al, *J. Neurochem.*, 1985, 44, 1615. Furthermore, they were tested with respect to their 5-HT reuptake inhibiting effect by measuring their ability to inhibit the uptake of $^3$H-serotonin in rat brain synapsomes in vitro by the method described by Hyttel and Larsen, *Acta Pharmacol. Tox.*, 1986, 56, suppl. 1, 146–153.

In general, the compounds of the invention have been found potently to inhibit both the binding of tritiated 8-hydroxy-2-dipropylaminotetralin (8-OH-DPAT) to 5-HT$_{1A}$ receptors and the binding of $^3$H ketanserin to 5-HT$_{2A}$ receptors in vitro. Some compounds only bind to one of the two serotonin receptor subtypes, 5-HT$_{1A}$ or 5-HT$_{2A}$. In addition to these affects, a number of the compounds have proven to have the further advantage of a potent 5-HT reuptake inhibiting effect. So, for example the compounds wherein R$^1$ is acetyl, R$^2$ is H and Ar is 3-indolyl substituted with halogen in the 6-position or 5-position or compounds wherein Ar is phenyl substituted with Cl in the 4-position show IC$_{50}$ values in the lower nanomolar range (1–65 nM).

Accordingly, the compounds of the invention are considered useful in the treatment of positive and negative symptoms of schizophrenia, other psychoses, anxiety disorders, such as generalised anxiety disorder, panic disorder, and obsessive compulsive disorder, depression, alcohol abuse, impulse control disorders aggression, side effects Induced by conventional antipsychotic agents, ischaemic disease states, migraine, senile dementia and cardiovascular disorders and in the improvement of sleep.

FORMULATION EXAMPLES

The pharmaceutical formulations of the invention may be prepared by conventional methods in the art.

For example: Tablets may be prepared by mixing the active ingredient with ordinary adjuvants and/or diluents and subsequently compressing the mixture In a conventional tabletting machine. Examples of adjuvants or diluents comprise: corn starch, potato starch, talcum, magnesium stearate, gelatine, lactose, gums, and the like, Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilization of the solution and filling in suitable ampules or vials. Any suitable additive conventionally used in the art may be added, such as tonicity agents, preservatives, antioxidants, etc. Typical examples of recipes for the formulation of the invention are as follows:

1) Tablets containing 5.0 mg of Compound 4a calculated as the free base:

| | |
|---|---|
| Compound 4a | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magneslum stearate | 0.84 mg |

2) Tablets containing 0.5 mg of Compound 4d calculated as the free base:

| | |
|---|---|
| Compound 4d | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per milliliter:

| | |
|---|---|
| Compound 11f | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 ml |

-continued

| Flavour | 0.05 mg |
| Saccharin natrium | 0.5 mg |
| Water | ad 1 ml |

4) Solution for injection containing per milliliter:

| Compound 4a | 0.5 mg |
| Sorbitol | 5.1 mg |
| Acetic acid | 0.08 mg |
| Water for injection | ad 1 ml |

What is claimed is:

1. A 4-aryl-1-(indanmethyl, dihydrobenzofuran-methyl or dihydrobenzothiophenemethyl) piperazine compound of Formula I

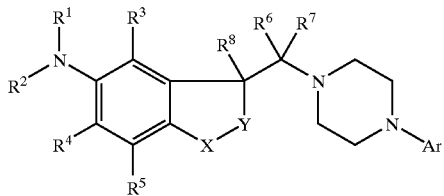

wherein one of X and Y is $CH_2$ and the other is O;

Ar is selected from the group consisting of phenyl, 2-thienyl, 3-thienyl, 2-furanyl, 3-furanyl, 2-pyrimidyl, 1-indolyl, 2-indolyl, 3-indolyl, 1-indol-2-onyl, 3-indol-2-onyl, 2-benzofuranyl, 3-benzofuranyl, 2-benzothiophenyl, 3-benzothiophenyl, 1-naphthyl, 2-naphthyl, wherein each Ar group can be optionally substituted with halogen, lower alkyl, lower alkoxy, lower alkylthio, hydroxy, lower alkylsulfonyl, cyano, trifluoromethyl, trifluoromethylsulfonyloxy, cycloalkyl, cycloalkyl-lower-alkyl, nitro, amino, lower alkylamino, di-lower alkylamino, acylamino or $C_{1-2}$ alkylenedioxy;

$R^1$ is selected from the group consisting of hydrogen, lower alkyl, lower alkenyl, lower alkynyl, cycloalk(en)yl, cycloalk(en)yl-lower alk(enlyn)yl, aryl, aryl-lower alkyl, acyl, thioacyl, lower alkylsulfonyl, trifluoromethylsulfonyl, and arylsulfonyl; or $R^1$ is a group $R^9VCO-$ where V is O or S and $R^9$ is lower alkyl, cycloalkyl, cycloalkyl-lower-alkyl or aryl, or $R^1$ is a group $R^{10}R^{11}NCO—$ or $R^{10}R^{11}NCS—$ wherein $R^{10}$ and $R^{11}$ are independently selected from the group consisting of hydrogen, lower alkyl, cycloalkyl, cycloalkyl-lower-alkyl and aryl, or $R^{10}$ and $R^{11}$ taken together with the N-atom to which they are linked, form a pyrrolidinyl, piperidinyl or perhydroazepin group;

$R^2$ is hydrogen, lower alkyl, cycloalkyl or cycloalkyl-lower-alkyl; or $R^1$ and $R^2$ taken together with the N-atom to which they are linked form a group,

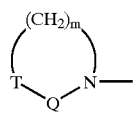

wherein Q is C=O, C=S or $CH_2$; T is NH, S, O or $CH_2$; and m is 1–4, inclusive;

$R^3-R^5$ are independently selected from the group consisting of hydrogen, halogen, lower alkyl, lower alkylcarbonyl, phenylcarbonyl, halogen substituted phenylcarbonyl, lower alkoxy, lower alkylthio, hydroxy, lower alkylsulfonyl, cyano, trifluoromethyl, cycloalkyl, cycloalkyl-lower-alkyl and nitro;

$R^6$ and $R^7$ are each hydrogen or lower alkyl or they can be linked together to form a 3–7 membered carbocyclic ring;

$R^8$ is hydrogen or lower alkyl;

any alkyl, cycloalkyl or cycloalkylalkyl group present can be optionally substituted with one or two hydroxy groups, which can be optionally esterified with an aliphatic or aromatic carboxylic acid; and any aryl substituent present can be optionally substituted with halogen, lower alkyl, lower alkoxy, lower alkylthio, hydroxy, lower alkylsulfonyl, cyano, trifluoromethyl, trifluromethylsulfonyloxy, cycloalkyl, cycloalkyl-lower-alkyl or nitro; or a pharmaceutically acceptable acid addition salt thereof.

2. A compound of claim 1, wherein $R^1$ is acyl, lower alkyl, lower alkoxy, a group $R^{10}R^{11}NCO—$ or $R^{10}R^{11}NCS—$ wherein $R^{10}$ is hydrogen, lower alkyl, cycloalkyl, cycloalkyl-lower-alkyl or aryl and $R^{11}$ is hydrogen or lower alkyl or $R^{10}$ and $R^{11}$ taken together with the N-atom to which they are linked, form a pyrrolidinyl, piperidinyl or perhydroazepin group.

3. A compound of claim 2, wherein $R^1$ is formyl, acetyl, methylaminocarbonyl, methylaminothiocarbonyl, dimethylaminocarbonyl, dimethylaminothiocarbonyl, methylsulfonyl, aminocarbonyl, cyclopropylcarbonyl, methyl, pyrrolidinylcarbonyl or 4-fluorophenylaminocarbonyl.

4. A compound of claim 1, wherein $R^2$ is hydrogen or lower alkyl.

5. A compound of claim 1, wherein $R^1$ and $R^2$ are linked together to form a 5–7 membered unsubstituted ring or a pyrrolidinyl, piperidinyl or perhydroazepin ring.

6. A compound of claim 1, wherein $R^3-R^5$ are hydrogen, fluoro, chloro, bromo, methyl, trifluoromethyl or acetyl and $R^6-R^8$ are hydrogen.

7. A compound of claim 1, wherein Ar is phenyl, 3-indolyl, 1-indolyl, or pyrimidyl substituted with halogen.

8. A compound of claim 1, wherein $R^1$ is acetyl, $R^2$ is H and Ar is 1-indolyl, 2-indolyl, 3-indolyl or phenyl substituted with halogen.

9. A compound of claim 8 wherein Ar is 3-indolyl substituted in the 5-position or 6-position with chloro, fluoro, or phenyl substituted in the 4-position with chloro.

10. A pharmaceutical composition comprising one or more compound of claim 1 in a therapeutically effective amount and in combination with one or more pharmaceutically acceptable carriers or diluents.

11. A method for treatment of psychoses, anxiety disorders, alcohol abuse, impulse control disorders, aggression, side effects induced by conventional antipsychotic agents, ischemic disease states, migraine, senile dementia, cardiovascular disorders, and for the improvement of sleep, obsessive compulsive disorder and depression, comprising administering to a patient in need of said treatment a pharmaceutical composition of claim 10.

12. A method of claim 11, wherein the psychosis is selected from the group consisting of positive symptoms of schizophrenia, and negative symptoms of schizophrenia.

13. A method of claim 11, wherein the anxiety disorder is selected from the group consisting of generalized anxiety disorder, and panic disorder.

14. A method of treating schizophrenia, comprising administering to a patient in need of said treatment a pharmaceutical composition of claim 10.

* * * * *